United States Patent [19]

Fiers et al.

[11] Patent Number: 5,004,689
[45] Date of Patent: Apr. 2, 1991

[54] DNA SEQUENCES, RECOMBINANT DNA MOLECULES AND PROCESSES FOR PRODUCING HUMAN GAMMA INTERFERON-LIKE POLYPEPTIDES IN HIGH YIELDS

[75] Inventors: Walter C. Fiers, Destelbergen, Belgium; Bernard Allet, Onex, Switzerland

[73] Assignee: Biogen, Massachusetts, Cambridge, Mass.

[21] Appl. No.: 31,042

[22] Filed: Mar. 27, 1987

Related U.S. Application Data

[63] Continuation-in-part of Ser. No. 920,720, Oct. 17, 1986, abandoned, which is a continuation of Ser. No. 722,743, Apr. 12, 1985, abandoned, which is a continuation of Ser. No. 467,466, Feb. 17, 1983, abandoned, which is a continuation-in-part of Ser. No. 800,069, Nov. 14, 1985.

[30] Foreign Application Priority Data

| Feb. 22, 1982 | [GB] | United Kingdom | 8205203 |
| Mar. 16, 1984 | [GB] | United Kingdom | 8406910 |
| May 24, 1984 | [GB] | United Kingdom | 8413297 |

[51] Int. Cl.$^5$ .................. C12P 21/00; C12N 1/20; C12N 15/00
[52] U.S. Cl. .................. 435/69.51; 435/252.3; 435/252.33; 435/320.1; 935/11; 935/44; 935/46; 935/73
[58] Field of Search .......... 435/6, 68, 70, 71, 91, 435/172.1, 172.3, 252.3, 252.31-252.35, 317, 243, 240.1, 240.2, 811, 320, 69.51; 436/63, 94; 935/11, 29, 78, 72-75, 66-71, 33.34, 38, 44, 46; 800/1; 530/351

[56] References Cited

U.S. PATENT DOCUMENTS

| 4,332,892 | 6/1982 | Ptashne et al. | 435/172.3 |
| 4,338,397 | 7/1982 | Gilbert et al. | 435/172.3 |
| 4,358,535 | 11/1982 | Falkow et al. | 435/6 |
| 4,727,138 | 2/1988 | Goeddel et al. | 435/91 |

OTHER PUBLICATIONS

Gray et al.; Nature 295: 503 (1982).
Vilcek; in Interferon-4, 1982, Academic Press, pp. 129-154.
Devos et al.; Nucleic Acids Res. 10: 2487 (1982).
Fiers et al.; Chem. Abstr. 98: 1180u (1983) of Philos. Trans. R. Soc. B, 299: 29 (1982).
Tanaka et al.; Chem Abstr. 98: 84343y (1983) of Nucleic Acids Symp. Ser., 1982, 11: 29-32.
Simonsen et al.; Chem. Abstr. 98: 1188c (1983) of UCLA Symp. Mol. Cell. Biol., 1982, 25: 1-14.
Genetic Engineering Letter 2(17), 1982.
McGraw-Hill's Biotechnology Newswatch 2(19), 5 (1982).
Maniatis et al.: Molecular Cloning a Laboratory Manual, 1982, Cold Spring Harbor Laboratory, pp. 405-406.
Grunstein et al.: Proc. Natl. Acad. Sci. U.S.A. 72: 3961 (1975).
Gray et al.; Nature 298: 859 (1982).

*Primary Examiner*—James Martinell
*Attorney, Agent, or Firm*—James F. Haley, Jr.; Leon R. Yankwich

[57] ABSTRACT

DNA sequences, recombinant DNA molecules and hosts transformed with them which produce polypeptides displaying a biological or immunological activity of gamma interferon. The genes coding for these polypeptides and methods of making and using these DNA sequences, molecules, hosts, genes and polypeptides are disclosed. The DNA sequences of this invention are further characterized by expression control sequences which permit the production of gamma interferon in high yields. More particularly, these expression control sequences comprise the λ P$_L$ promoter, and more preferably, a trp-derived expression control sequence containing the sequence ATCGATACT between the Shine-Dalgarno sequence and the translational start signal. In appropriate hosts, these DNA sequences and recombinant DNA molecules permit the production and identification of genes and polypeptides displaying a biological or immunological activity of gamma interferon and their use in antiviral, antitumor or anticancer, and immunomodulation agents and methods.

12 Claims, 12 Drawing Sheets

FIG. 7

```
                                                                                                                      Met
A GAA AGA TCA GTT AAG TCC TTT GGA CCT GAT CAG CTT GAT ACA AGA ACT ACT GAT TTC AAC TTT GGC TTA ATT CTC TCG GAA ACG ATG   91

-10                                              -1
Lys Tyr Thr Ser Tyr Ile Leu Ala Phe Gln Leu Cys Ile Val Leu Gly Ser Leu Gly Cys Tyr Cys Gln Asp Pro Tyr Val Lys Glu Ala
AAA TAT ACA AGT TAT ATC TTG GCT TTT CAG CTC TGC ATC GTT TTG GGT TCT CTT GGC TGT TAC TGC CAG GAC CCA TAT GTA AAA GAA GCA   181
                    20                                        30                                         40
Glu Asn Leu Lys Tyr Phe Asn Ala Asp Val Ala Asp Asn Gly Thr Leu Phe Leu Gly Ile Leu Lys Leu Asn Trp Lys Lys Glu
GAA AAC CTT AAG AAA TAT TTT AAT GCA GAT GTA GCG GAT AAT GGA ACT CTT TTC TTA GGC ATT TTG AAG AAT TGG AAA GAG   271
                    50                                        60                                         70
Glu Ser Asp Arg Lys Ile Met Gln Ile Met Ser Gln Ile Val Ser Phe Tyr Phe Lys Leu Asn Phe Lys Asp Asp Gln Ser Ile Gln Lys
GAG AGT GAC AGA AAA ATA ATG CAG ATA ATG AGC CAA ATT GTC TCC TTT TAC TTC AAA CTT AAT TTT AAA GAT GAC CAG AGC ATC CAA AAG   361
                    80                                        90                                        100
Ser Val Glu Thr Ile Lys Glu Asp Met Asn Lys Val Lys Phe Phe Asn Ser Asn Lys Leu Lys Arg Asp Asp Phe Glu Lys Leu Thr Asn Tyr
AGT GTG GAG ACC ATC AAG GAA GAC ATG AAT AAA GTC AAG TTT TTC AAT AGC AAT AAG AAA CGA GAT GAC TTC GAA AAG CTG ACT AAT TAT   451
                   110                                       120                                        130
Ser Val Thr Asp Leu Asn Val Gln Arg Lys Ala Ile Ile His Glu Leu Ile Gln Val Met Ala Glu Leu Ser Pro Ala Ala Lys Thr Gly Lys
TCG GTA ACT GAC TTG AAT GTC CAA CGC AAA GCA ATA CAT GAA CTC ATC CAA GTG ATG GCT GAA CTG TCG CCA GCA GCT AAA ACA GGG AAG   541
                   140                                         146
Arg Lys Arg Ser Gln Met Leu Phe Arg Gly Arg Arg Ala Ser Gln
CGA AAA AGG AGT CAG ATG CTG TTT CGA GGT CGA AGA GCA TCC CAG TAA TGG TTG TCC TGC CTG CAA TAT TTG AAT TTT AAA TCT   631

ATT TAT TAA TAT ACA TTA TTT ATA TGG GGA ATA TAT TTT TAG ACT CAT CAA TCA AAT AAG TAT TTA TAA CAA CTT TTG TGT AAT   721

GAA AAT GAA TAT CTA TTA ATA TAT GTA TTA TTT ATA ATT CCT ATA TCC TGT GAC TGT CTC ACT TAA TCC TTT GTT TTC TGA CTA ATT AGG   811

CAA GGC TAT GTG ATT ACA AGG CTT TAT CTC AGG GGC CAA CTA GGC AGC CAA CCT AAG CAA GAT CCC ATG GGT TGT GTG TTT ATT TCA CTT   901
```

FIG.8

GAT GAT ACA ATG AAC ACT TAT AAG TGA AGT GAT ACT ATC CAG TTA CTG CCG GTT TGA AAA TAT GCC TGC AAT CTG AGC CAG TGC TTT AAT 991

GGC ATG TCA GAC AGA ACT TGA ATG TGT CAG GTG ACC CTG ATG AAA ACA TAG CAT CTC AGG AGA TTT CAT GCC TGG TGC TTC CAA ATA TTG 1081

TTG ACA ACT GTG ACT GTA CCC AAA TGG AAA GTA ACT CAT TTG TTA AAA TTG GGG GGG GGG GGG 1144

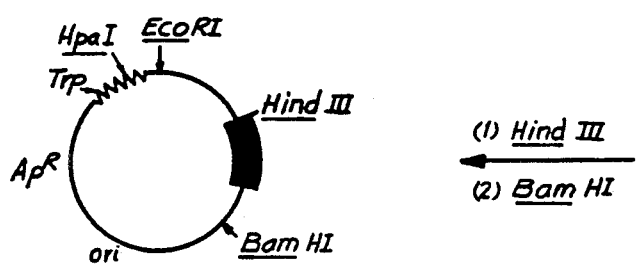
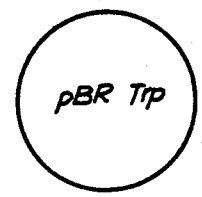
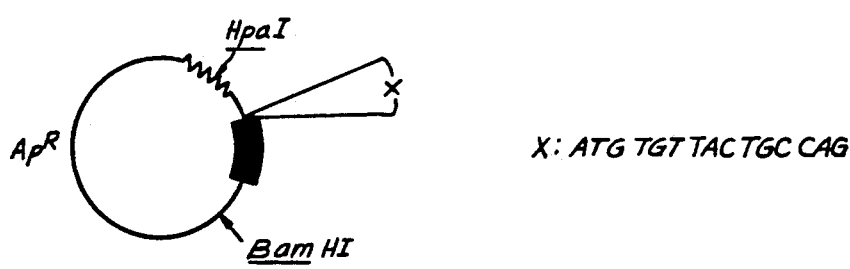
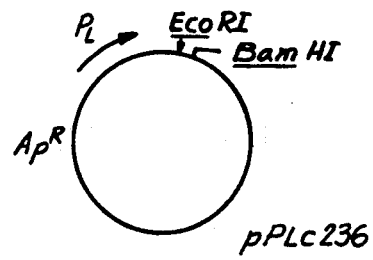
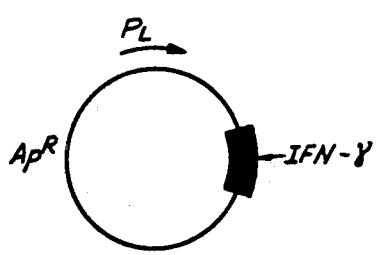
FIG.9

FIG. 10
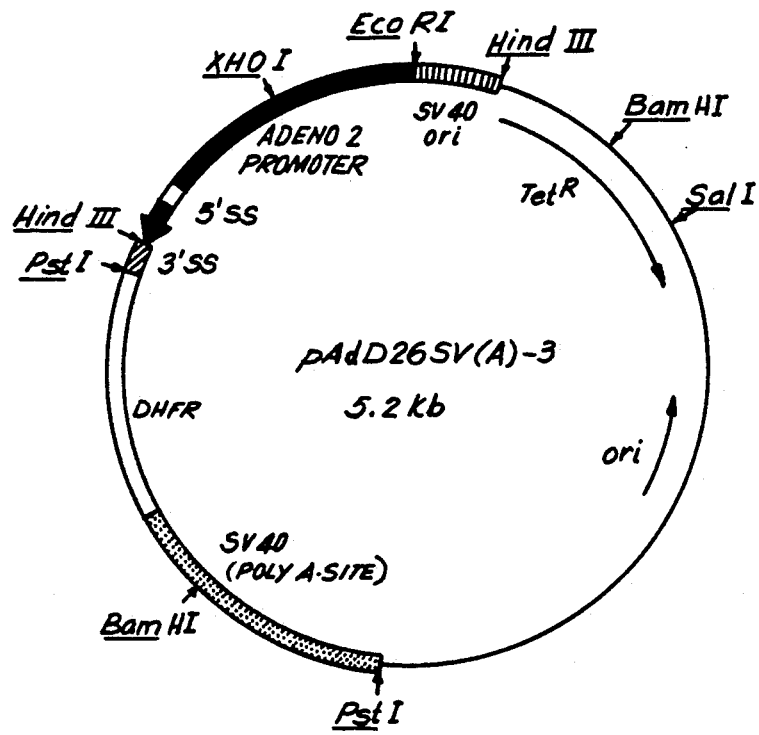
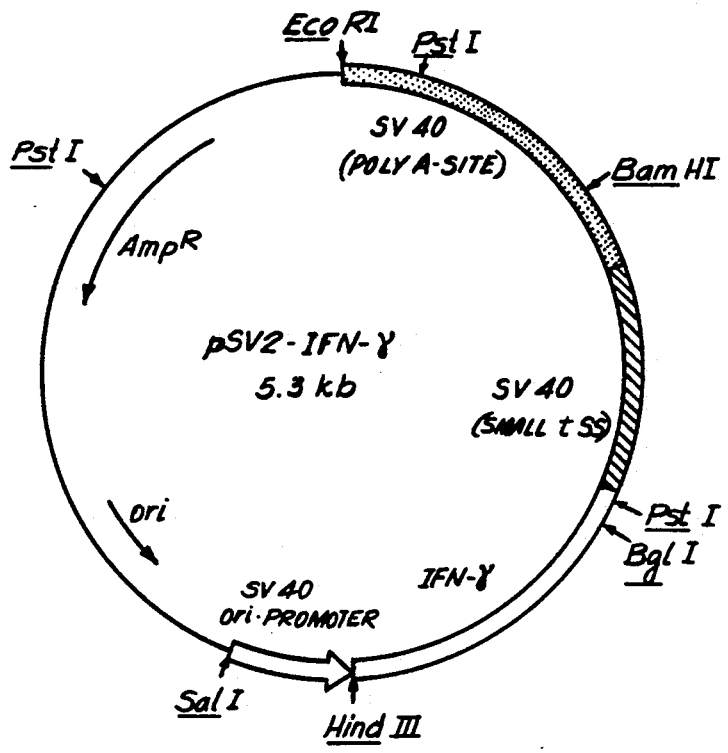

FIG. 12

DNA SEQUENCES, RECOMBINANT DNA MOLECULES AND PROCESSES FOR PRODUCING HUMAN GAMMA INTERFERON-LIKE POLYPEPTIDES IN HIGH YIELDS

This is a continuation-in-part of application Ser. No. 920,720, filed Oct. 17, 1986 and now abandoned, which is a continuation of application Ser. No. 722,743, filed Apr. 12, 1985 and now abandoned, which is a continuation of application Ser. No. 467,466, filed Feb. 17, 1983 now abandoned, entitled "DNA Sequences, Recombinant DNA Molecules And Processes For Producing Human Immune Interferon-Like Polypeptides; and a continuation-in-part of copending application Ser. No. 800,069, filed Nov. 14, 1985, entitled "A Modified Gamma Interferon, DNA Sequences Encoding It And Processes For Producing It," which was filed as PCT application PCT/EP85/00109 on Mar. 16, 1985.

TECHNICAL FIELD OF INVENTION

This invention relates to DNA sequences, recombinant DNA molecules and processes for producing gamma interferon-like polypeptides. More particularly, the invention relates to DNA sequences expressed in appropriate host organisms. The recombinant DNA molecules disclosed herein are characterized by DNA sequences that code for polypeptides which have an immunological or biological activity of gamma interferon. As will be appreciated from the disclosure to follow, the DNA sequences, recombinant DNA molecules and processes of this invention may be used in the production of polypeptides useful in antiviral and antitumor or anticancer and immunomodulation agents and methods.

The invention also relates to expression control systems and method for using them to improve the expression levels of the DNA sequences encoding gamma interferon-like polypeptides. More particularly, the invention relates to the λ $P_L$ temperatureinducible expression system and, more preferably, to the promoter and operator regions derived from a tryptophan (trp) operon, for the production of high levels of gamma interferon-like polypeptides.

BACKGROUND ART

In this application we will use the interferon nomenclature announced in Nature, 286, p. 110 (July 10, 1980). "IFN" will designate interferon and "IFN-γ" will designate gamma interferon, formerly known as "immune" interferon.

Two classes of interferon ("IFN") are known to exist. Interferons of type I are small, acid stable proteins that render cells resistant to viral infection (A. Isaacs and J. Lindenmann, "Virus Interference I. The Interferon", *Proc. Royal Soc. Ser. B.*, 147, pp. 258–67 (1957); W. E. Stewart II, *The Interferon System*, Springer-Verlag (2 ed.) (1981) (hereinafter "The Interferon System")). Type II IFNs are acid labile. At present, they are poorly characterized. Although rather cell specific (*The Interferon System*, pp. 135–45), IFNs are not virus specific. IFNs protect cells against a wide spectrum of viruses.

Type II interferons can be produced spontaneously, or in response to various inducers, such as viruses, microorganisms, mitogens, viral or bacterial antigens, or in response to antibiotics, endotoxins or other microbial products (*The Interferon System*, pp. 148–49). Most usually, mitogens such as Staphylococcal enterotoxin, galactose oxidase, phytohemagglutinin, concanavalin, Corynebacterium parvum and mixed lymphocyte cultures are used. Type II interferons have also been reported to be produced from a variety of sources; for example, cerebrospinal fluid in CNS disease, leukocytes induced with phytohemagglutinin, lymphocytes induced with antilymphocyte serum, lymphocytes induced with macrophages and mitogens, tonsil lymphocytes induced with mitogens, herpes-sensitized lymphocytes induced with macrophages and herpes virus antigen, rubella-virus sensitized lymphocytes induced with rubella virus, lymphoblastoid cells, bone marrow of multiple myeloma patients, lymphocytes from a leukemic T-cell line and lymphocytes isolated from buffy coats, human milk or by plasmaphoresis (*The Interferon System*, pp. 146–47; I. Nathan et al., "Immune (γ) Interferon Produced By A Human T-Lymphoblast Cell Line", *Nature*, 292, pp. 842–43 (1981); M. A. Heller et al., "Lymphokine Production By Human Milk Lymphocytes", *Infection And Immunity*, 32, pp. 632–36 (1981); G. R. Klimpel et al., "Differential Production Of Interferon And Lymphotoxin By Human Tonsil Lymphocytes", *Cellular Immunity*, 20, pp. 187–96 (1975); M. DeLey et al., "Interferon Induced In Human Leucocytes By Mitogens: Production, Partial Purification And Characterization", *Eur. J. Immunol.*, 10, pp. 877–83 (1980); M. Wiranowska-Stewart and W. E. Stewart II, "Determination Of Human Leukocyte Population Involved In Production Of Interferon Alpha And Gamma", *J. Interferon Research*, 1, pp. 233–44 (1981)). Considering this heterogeneity, Type II IFN production upon mitogenic stimulation appears to depend upon the source of the lymphocytes and upon the isolation procedure employed.

Interferon therapy against viruses and tumors or cancers has been conducted at varying dosage regimes and under several modes of administration (*The Interferon System*, pp. 306–22). For example, interferon has been effectively administered orally, by inoculation—intravenously, intramuscularly, intranasally, intradermally and subcutaneously—and in the form of eye drops, ointments and sprays. It is usually administered one to three times daily in dosages of $10^4$ to $10^8$ units. The extent of the therapy depends on the patient and the condition being treated. For example, virus infections are usually treated by daily or twice daily doses over several days to two weeks and tumors and cancers are usually treated by daily or multiple daily doses over several months or years. The most effective therapy for a given patient must of course be determined by the attending physician, who will consider such well known factors as the course of the disease, previous therapy, and the patient's response to interferon in selecting a mode of administration and a dosage regime.

As an antiviral agent, human interferon ("HuIFN") has been used to treat the following: respiratory infections (*Texas Reports*, pp. 486–96); herpes simplex keratitis (*Texas Reports*, pp. 497–500; R. Sundmacher, "Exogenous Interferon In Eye Diseases", *International Virology IV*, The Hague, Abstract nr. w2/11, p. 99 (1978)); acute hemorrhagic conjunctivitis (*Texas Reports*, pp. 501–10); adenovirus keratoconjunctivitis (A. Romano et al., ISM Memo I-A8131 (October, 1979)); varicella zoster (*Texas Reports*, pp. 511–15); cytomegalovirus infection (*Texas Reports*, pp. 523–27); and hepatitis B (*Texas Reports*, pp. 516–22). See also *The Interferon System*, pp. 307–21. However, large-scale use of IFN as an antiviral agent requires larger amounts of IFN than heretofore have been available.

IFN has other effects in addition to its antiviral action. For example, it antagonizes the effect of colony-stimulating factor, inhibits the growth of hemopoietic colony-forming cells and interferes with the normal differentiation of granulocyte and macrophage precursors (*Texas Reports*, pp. 343-49). It also inhibits erythroid differentiation in DMSO-treated Friend leukemia cells (*Texas Reports*, pp. 420-28).

IFN may also play a role in regulation of the immune response. For example, depending upon the dose and time of application in relation to antigen, IFN can be both immunopotentiating and immunosuppressive in vivo and in vitro (*Texas Reports*, pp. 357-69). In addition, specifically sensitized lymphocytes have been observed to produce IFN after contact with antigen. Such antigen-induced IFN could therefore be a regulator of the immune response, affecting both circulating antigen levels and expression of cellular immunity (*Texas Reports*, pp. 370-74). IFN is also known to enhance the activity of killer lymphocytes and antibody-dependent cell-mediated cytotoxicity (R. R. Herberman et al., "Augmentation By Interferon Of Human Natural And Antibody-Dependent Cell-Mediated Cytotoxicity", *Nature*, 227, pp. 221-23 (1979); P. Beverley and D. Knight, "Killing Comes Naturally", *Nature*, 278, pp. 119-20 (1979); *Texas Reports*, pp. 375-80; J. R. Huddlestone et al., "Induction And Kinetics Of Natural Killer Cells In Humans Following Interferon Therapy", *Nature*, 282, pp. 417-19 (1979); S. Einhorn et al., "Interferon And Spontaneous Cytotoxicity In Man. II. Studies In Patients Receiving Exogenous Leukocyte Interferon", *Acta Med. Scand.* 478-83 (1978)).

Killer lymphocytes and antibody-dependent cell-mediated cytotoxicity may be directly or indirectly involved in the immunological attack on tumor cells. Therefore, in addition to its use as an antiviral agent, IFN has potential application in antitumor and anticancer therapy and in immunomodulation agents and methods (*The Interferon System*, pp. 319-21, 394-99). It is now known that IFNs affect the growth of many classes of tumors in many animals (*The Interferon System*, pp. 292-304). Interferons, like other antitumor agents, seem most effective when directed against small tumors. The antitumor effects of animal IFN are dependent on dosage and time, but have been demonstrated at concentrations below toxic levels. Accordingly, numerous investigations and clinical trials have been and continue to be conducted into the antitumor and anticancer properties of HuIFNs. These include treatment of several malignant diseases such as osteosarcoma, acute myeloid leukemia, multiple myeloma and Hodgkin's disease (*Texas Reports*, pp. 429-35). Although the results of these clinical tests are encouraging, the antitumor, anticancer and immunomodulation applications of IFNs have been severely hampered by lack of an adequate supply of purified IFN.

At the biochemical level, IFNs induce the formation of at least three proteins: a protein kinase (B. Lebleu et al., "Interferon, Double-Stranded RNA And Protein Phosphorylation", *Proc. Natl. Acad. Sci. USA*, 73, pp. 3107-11 (1976); A. G. Hovanessian and I. M. Kerr, "The (2'-5') Oligoadenylate (ppp A2'-5A2'-5'A) Synthetase And Protein Kinase(s) From Interferon-Treated Cells", *Eur. J. Biochem.*, 93, pp. 515-26 (1979)), a (2'-5')oligo(A) synthetase (A. G. Hovanessian et al., "Synthesis Of Low-Molecular Weight Inhibitor Of Protein Synthesis With Enzyme From Interferon-Treated Cells", *Nature*, 268, pp 537-39 (1977); A. G. Hovanessian and I. M. Kerr, *Eur. J. Biochem.*, supra) and a phosphodiesterase (A. Schmidt et al., "An Interferon-Induced Phosphodiesterase Degrading (2'-5') Oligoisoadenylate And The C-C-A Terminus Of tRNA", *Proc. Natl. Acad. Sci. USA*, 76, pp. 4788-92 (1979)).

Interferons have been classified into three groups—α, β and γ. Of these, α and β interferons are acid stable, type I interferons, while γ-interferon is an acid labile, type II interferon. In addition, the three IFNs are antigenically distinct from each other.

IFN-α and IFN-β are better characterized than IFN-γ. IFN-γ is reported to be a glycoprotein (A. Mizrami et al., "Glycosylation Of Interferon", *J. Biol. Chem.*, 253, pp. 7612-15 (1978); M. P. Langford et al., "Large-Scale Production And Physicochemical Characterization Of Human Immune Interferon", *Infection And Immunity*, 26, pp. 36-41 (1979); *The Interferon System*, pp. 107-08). It has also been reported to have a molecular weight of 40,000-46,000 daltons, with the possibility that its glycosylated form has a molecular weight of 65,000-70,000 daltons. In addition to being acid labile (at pH 2), IFN-γ has been reported to be inactivated after 1 h at 56° C. See also DeLey et al., supra; Y. K. Yip et al., "Partial Purification And Characterization Of Human γ (Immune) Interferon", *Proc. Natl. Acad. Sci. USA*, 78, pp. 1601-605 (1981); M. P. Langford et al., "Large-Scale Production And Physicochemical Characterization Of Human Immune Interferon", *Infection And Immunity*, 26, pp. 36-41 (1979). And, it has been reported that IFN-γ recognizes a different cell receptor than IFN-α or IFN-β (A. A. Branca and C. Baglioni, "Evidence That Types I And II Interferons Have Different Receptors", *Nature*, 294, pp. 768-70 (1981)).

In addition to its antiviral activity, IFN-γ is reported to display antitumor activity. Moreover, as compared to IFN-α and IFN-β, IFN-γ's antitumor activity seems, at least in mice, to result in tumor regression. In addition, its activation of natural killer cells does not reach a plateau as observed for IFN-α and IFN-β and IFN-γ appears to be less inhibited by circulating levels of gangliosides than are IFN-α and IFN-β (H. Ankel et al., "Mouse Fibroblast (Type I) And Immune (Type II) Interferons: Pronounced Differences In Affinity For Gangliosides And In Antiviral And Antigrowth Effects On Mouse Leukemia L-1210R Cells", *Proc. Natl. Acad. Sci. USA*, 77, pp. 2528-32 (1980)). Therefore, it appears that cells or tumors that display a poor response to IFN-α or IFN-β may be effectively treated with IFN-γ (e.g., Crane et al., *J. Natl. Cancer Institute*, 61, p. 891 (1978); Barn et al., *Abstract N.Y. Acad. Sci.*, No. 11 (Oct. 23-26, 1979); Blalock et al., *Cellular Immunology*, 49, pp. 390-94 (1980); B. Y. Rubin and S. L. Gupta, "Differential Efficacies Of Human Type I And Type II Interferons As Antiviral And Antiproliferative Agents", *Proc. Natl. Acad. Sci. USA*, 77, pp. 5928-32 (1980)).

Another use of IFN-γ may be as an immunoregulatory agent. IFN-γ has been found to be useful in treating rheumatoid arthritis and in the treatment of certain allergies. IFN-γ is also useful in combination with other compounds. For example, when combined with tumor necrosis factor ("TNF") tumor growth is inhibited beyond that seen with IFN-γ or TNF alone (see European patent application 131,789). IFN-γ can also be combined with other lymphokines, such as IFN-α, IFN-β and Interleukin 2, or with anti-inflammatories for enhanced effect.

HuIFN-γ, like many human proteins, may also be polymorphic. Therefore, cells of particular individuals may produce IFN-γ species within the more general IFN-γ class which are physiologically similar but structurally slightly different from the prototype of the class of which it is a part. Therefore, while the protein structure of the IFN-γ may be generally well-defined, particular individuals may produce IFN-γ's that are slight variations thereof.

Both a family of HuIFN-α's and a HuIFN-β have been produced in appropriate hosts using recombinant DNA technology (e.g., S. Nagata et al., "Synthesis In E. coli Of A Polypeptide With Human Leukocyte Interferon Activity", Nature, 284, pp. 316-20 (1980) (IFN-α) and R. Derynck et al., "Expression Of The Human Fibroblast Interferon Gene In Escherichia coli", Nature, 287, pp. 193-202 (1980) (IFN-β)). Such techniques have allowed further characterization and initial clinical trials of the HuIFN-α and HuIFN-β.

Today, the extremely small quantities of HuIFN-γ that are available are produced by a human cell line grown in tissue culture or more usually from leukocytes collected from blood samples. These processes are low yield and expensive ones. They have not provided sufficient HuIFN-γ to permit further characterization or clinical trials to elucidate further the antiviral, antitumor or immunomodulation activities of IFN-γ or to compare those activities to the antiviral, antitumor and immunomodulation activities of IFN-α and IFN-γ.

DISCLOSURE OF THE INVENTION

The present invention solves the problems referred to by locating and separating DNA sequences that code for IFN-γ and transforming appropriate hosts with those sequences thereby providing DNA sequences, recombinant DNA molecules and methods for the use of those sequences and molecules in the production of polypeptides displaying an immunological or biological activity of gamma interferon. Furthermore, this invention provides DNA sequences which enhance the expression levels of gamma interferon in hosts transformed with the gene encoding IFN-γ.

By virtue of this invention, it is possible to obtain polypeptides displaying an immunological or biological activity of IFN-γ for use in antiviral, antitumor, anticancer or immunomodulation agents and methods. This invention allows the production of these polypeptides in amounts and by methods hitherto not available.

As will be appreciated from the disclosure to follow, the DNA sequences and recombinant DNA molecules of the invention are capable of directing the production in an appropriate host of polypeptides displaying an immunological or biological activity of HuIFN-γ. Replication of these DNA sequences and recombinant DNA molecules in appropriate hosts also permits the production in large quantities of genes coding for these polypeptides. The molecular structure and properties of these polypeptides and genes may thus be readily determined. The polypeptides and genes are useful, either as produced in the host or after appropriate derivatization or modification, in compositions and methods for detecting and improving the production of these products themselves and for use in antiviral, antitumor, anticancer or immunomodulation agents and methods.

It will be appreciated from the foregoing that a basic aspect of this invention is the provision of a DNA sequence which is characterized in that it codes for a polypeptide displaying an immunological or biological activity of HuIFN-γ, or at least allows the selection of such sequences from a collection of DNA sequences, and is selected from the group consisting of the DNA inserts γ$_0$, γ$_1$, γ$_2$, γ$_3$, γ$_5$, γ$_6$, γ$_8$, γ$_9$, γ$_{10}$, γ$_{11}$, DNA sequences which hybridize to any of the foregoing DNA inserts, DNA sequences, from whatever source obtained, including natural, synthetic or semi-synthetic sources, related by mutation, including single or multiple, base substitutions, deletions, insertions and inversions to any of the foregoing DNA sequences or inserts, and DNA sequences comprising sequences of codons which on expression code for a polypeptide displaying similar immunological or biological activity to a polypeptide coded for on expression by the codons of any of the foregoing DNA sequences.

The sequences of this invention are further characterized in that they permit the production of HuIFN-γ and HuIFN-γ-like polypeptides in hosts in high yields. More particularly, the methods and recombinant DNA molecules of this invention utilize an expression control sequence comprising the γ P$_L$ promoter, and more preferably, the promoter and operator regions of a tryptophan (trp)-derived operon containing the sequence ATCGATACT between the Shine-Dalgarno sequence and the translational start signal, for the production of IFN-γ-like polypeptides. Most preferably the trp-derived DNA sequences are derived from E. coli. A particularly preferred expression control sequence comprises:

GGTGTCATGGTCGGTGATCGCCAGGGTGCCGACGCGC
ATCTCGACTGCACGGTGCACCAATGCTTCTGGCGTCA
GGCAGCCATCGGAAGCTGTGGTATGGCTGTGCAGGTC
GTAAATCACTGCATAATTCGTGTCGCTCAAGGCGCAC
TCCCGTTCTGGATAATGTTTTTTGCGCCGACATCATAA
CGGTTCTGGCAAATATTCTGAAATGAGCTGTTGACAA
TTAATCATCGAACTAGTTAACTAGTACGCAAGTTCACG
TAAAAAGGGTATCGATACT.

BRIEF DESCRIPTION OF THE DRAWINGS

FIGS. 7-8 display the nucleotide sequence of the coding strand of the composite DNA that codes for HuIFN-γ. The sequence is numbered from the beginning of the composite DNA well into the untranslated area of the composite DNA. Nucleotides 89-148 represent a signal sequence and nucleotides 149-586 apparently represent the "mature" IFN-γ. The amino acid sequences of the signal polypeptide and the mature IFN-γ are depicted above their respective nucleotide sequences, the amino acids of the signal polypeptide being numbered from −20 to −1 and the amino acids of the apparent mature IFN-γ being numbered 1 to 146.

FIG. 9 is a schematic representation of the construction of an expression vector capable of producing high levels of IFN-γ in a bacterial cell by expressing DNA sequences encoding IFN-γ-like polypeptides using the $P_L$ expression system.

FIG. 10 is a schematic representation of the plasmids pAdD26SV(A)-3 and pSV2-IFN-γ.

FIG. 12 is a depiction of the DNA sequence of a recombinant DNA molecule comprising the trp operon expression system and DNA sequences encoding IFN-γ, useful for producing high levels of IFN-γ in a bacterial cell.

BEST MODE OF CARRYING OUT THE INVENTION

Figure 1:
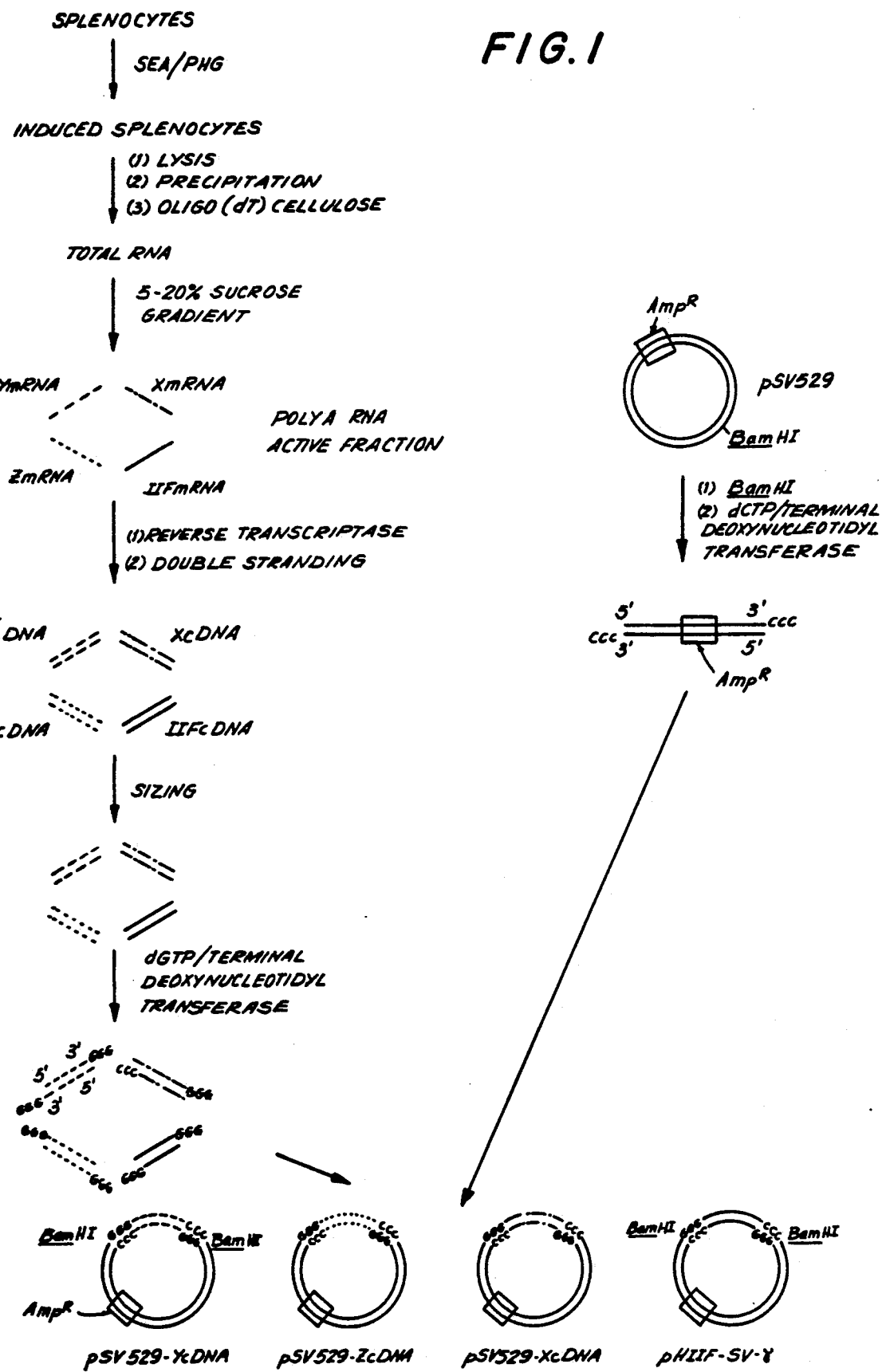
FIG. 1 is a schematic outline of one embodiment of a process of this invention for preparing a mixture of recombinant DNA molecules, some of which are characterized by inserted DNA sequences that code for the polypeptides of this invention.

In order that the invention herein described may be more fully understood, the following detailed description is set forth.

In the description the following terms are employed:

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C"), and thymine ("T"). The four RNA bases are A, G, C, and uracil ("U").

DNA Sequence—A linear array of nucleotides connected one to the other by phosphodiester bonds between the 3' and 5' carbons of adjacent pentoses.

Codon—A DNA sequence of three nucleotides (a triplet) which encodes through mRNA an amino acid, a translation start signal or a translation termination signal. For example, the nucleotide triplets TTA, TTG, CTT, CTC, CTA and CTG encode the amino acid leucine ("Leu"), TAG, TAA and TGA are translation stop signals and ATG is a translation start signal.

Reading Frame—The grouping of codons during the translation of mRNA into amino acid sequences. During translation the proper reading frame must be maintained. For example, the DNA sequence GCTGGTTGTAAG may be expressed in three reading frames or phases, each of which affords a different amino acid sequence:

GCT GGT TGT AAG—Ala—Gly—Cys—Lys

G CTG GTT GTA AG—Leu—Val—Val

GC TGG TTG TAA G—Trp—Leu-(STOP)

Polypeptide—A linear array of amino acids connected one to the other by peptide bonds between the α-amino and carboxy groups of adjacent amino acids.

Genome—The entire DNA of a cell or a virus. It includes, inter alia, the structural gene coding for the polypeptides of the substance, as well as operator, promoter and ribosome binding and interaction sequences, including sequences such as the Shine-Dalgarno sequences.

Structural Gene—A DNA sequence which encodes through its template or messenger RNA ("mRNA") a sequence of amino acids characteristic of a specific polypeptide.

Transcription—The process of producing mRNA from a structural gene.

Translation—The process of producing a polypeptide from mRNA.

Expression—The process undergone by a structural gene to produce a polypeptide. It is a combination of transcription and translation.

Plasmid—A nonchromosomal double-stranded DNA sequence comprising an intact "replicon" such that the plasmid is replicated in a host cell. When the plasmid is placed within a unicellular organism, the characteristics of that organism may be changed or transformed as a result of the DNA of the plasmid. For example, a plasmid carrying the gene for tetracycline resistance (Tet®) transforms a cell previously sensitive to tetracycline into one which is resistant to it. A cell transformed by a plasmid is called a "transformant".

Phage or Bacteriophage—Bacterial virus, many of which consist of DNA sequences encapsidated in a protein envelope or coat ("capsid").

Cloning Vehicle—A plasmid, phage DNA or other DNA sequence which is able to replicate in a host cell, characterized by one or a small number of endonuclease recognition sites at which such DNA sequences may be cut in a determinable fashion without attendant loss of an essential biological function of the DNA, e.g., replication, production of coat proteins or loss of promoter or binding sites, and which contain a marker suitable for use in the identification of transformed cells, e.g., tetracycline resistance or ampicillin resistance. A cloning vehicle is often called a vector.

Cloning—The process of obtaining a population of organisms or DNA sequences derived from one such organism or sequence by asexual reproduction.

Recombinant DNA Molecule or Hybrid DNA—A molecule consisting of segments of DNA from different genomes which have been joined end-to-end outside of living cells and able to be maintained in living cells.

Expression Control Sequence—A sequence of nucleotides that controls and regulates expression of structural genes when operatively linked to those genes. They include the lac system, major operator and promoter regions of phage γ, the control region of fd coat protein and other sequences known to control the expression of genes of prokaryotic or eukaryotic cells and their viruses or combinations thereof.

In order that this invention may be better understood, the following example is set forth. This example is for purposes of illustration only, and is not to be construed as limiting the scope of the invention.

Referring now to FIG. 1, we have shown therein a schematic outline of one embodiment of a process for preparing a mixture of recombinant DNA molecules, some of which include inserted DNA sequences that characterize this invention.

PREPARATION OF POLY(A) RNA CONTAINING

HUMAN GAMMA INTERFERON mRNA (IFN-γ mRNA)

The RNA used in this invention was extracted from mitogen-stimulated human splenocytes. Splenocytes offered to us the advantages that they provided a large quantity of immune system cells from a single donor and they also produced gamma interferon in amounts subject to less fluctuations due to a depletion of interleukin I producing cells because splenocytes are essentially composed of lymphocytes and macrophages. In our hands, splenocyte viability and the interferon titer depended mainly on the time between removal and processing of the spleen.

(a) Isolation Of Human Splenocytes

Human spleens obtained from surgical departments were transported to our laboratory in sterile plastic bags and once in the laboratory were transferred to sterile glass dishes. We removed the outer membrane of the spleen with sterile dissection scissors and thus excised 5 cm$^3$ of the spleen tissue. This tissue was placed in a plastic Petri dish (15 cm dia), where it was cut into still smaller pieces (of ~0.5 cm$^3$). After the addition of approximately 10 ml RPMI 1640 medium (Gibco) (supplemented with 2 g/l NaHCO$_3$ and 20 mM HEPES), we mashed the tissue fragments gently with the end of a plunger from a 2 ml plastic syringe until most of the cells were loosened. We then diluted the suspension with approximately 50 ml RPMI 1640 medium and thoroughly mixed the resulting suspension. We then transferred the tissue and cell suspension to a sterile metal sieve (8 x 0.3 mm/cm) and drained the liquid into another plastic Petri dish. We then returned the tissue on the sieve to the original plastic dish and mashed and filtered as before. Finally, we poured the total cell suspension into a 0.5–1 plastic tube. This procedure was repeated with fresh pieces until the whole spleen had been prepared.

We removed most of the dead cells, which aggregated and formed a thick precipitate on the bottom of the plastic tube, by filtering the suspension again through the metal sieve. We then transferred the cell suspension to 100-ml sterile conical siliconized glass centrifuge tubes and removed any aggregates still present at the bottom of the tubes or at the surface of the suspension.

We then collected the cells by centrifugation at room temperature for 10 min at 900 x g and lysed the erythrocytes by gently suspending the cells in 10 vol cold Tris-NH$_4$Cl (9 parts 0.83% NH$_4$Cl plus one part Tris-HCl, (20.6 g/l, pH 7.2)) solution. After 10 min at 4° C., any dead cells that had aggregated at the bottom were removed and the white cells were collected and washed at least twice with RPMI 1640 medium. We then took the cells up in complete medium (RPMI 1640 supplemented with 0.03% L-glutamine, 100 U/ml penicillin, 100 µg/ml streptomycin, 25 µg/ml neomycin, 5×10$^{-5}$M β-mercaptoethanol and 10% fetal calf serum) to a concentration of 2–4×10$^6$ cells/ml.

(b) Stimulation Of Human Splenocytes With Mitogen

We transferred the above-described cell suspension (~5 liters, 1×10$^{10}$ cells) to spinner flasks and added staphylococcus enterotoxin A ("SEA") (purified from staphylococcus aureus strain 13N2909 essentially as described by E. J. Schantz et al., "Purification And Some Chemical And Physical Properties Of Staphylococcal Enterotoxin A", *Biochemistry*, 11, pp. 360–66 (1972), and L. Spero and J. F. Metzger, "Staphylococcal Enterotoxin A (SEA)" in *Methods in Enzymology*, 79 (Pestka, S., ed.) (1982)) to a final concentration of 0.5 mg/ml and phytohemagglutinin ("PHA") to a concentration of 10 mg/ml. After saturation of the atmosphere above the culture with a 5% CO gas mixture, we slowly stirred the suspension at 37° C. for 2.5 days. After 2.5 days we assayed for IFN using an antiviral assay on T21 cells (trisomic for chromosome 21) (Y. H. Tan et al., "Human Chromosome 21 Dosage: Effect On The Expression Of The Interferon Induced Antiviral State", *Science*, 186, pp. 61–63, (1974) using encephalomyocarditis virus ("EMC") as the challenge virus (S. L. Berger et al., "Characterization Of Interferon Messenger RNA Synthesized In Namalva Cells", *J. Biol. Chem.*, 255, pp. 2955–61 (1980)). In that assay we observed an interferon titer of 3.5–4.0 (log$_{10}$ Lab. Units/ml).

Our assay is more sensitive than that using FS4 cells because one unit of the NIH leukocyte-IFN standard gives about 1.7 (log$_{10}$ Lab. Units/ml) in our assay. Accordingly, our results, reported in "Lab. Units", must be divided by a factor of about 50 to convert them into "International (leukocyte) units".

It should, of course, be understood that other mitogens could also be used to induce IFN-γ production in the splenocytes. For example, we have used SEA (0.5 µg/ml) alone and a mixture of PHA (10 µg/ml) and 12-0-tetradecanoylphorbol-13-acetate ("TPA"). Our results suggest that the amount of IFN produced is mainly dependent upon the quality of the splenocytes (i.e., the time between surgical removal and culturing of the cells).

(c) Isolation And Translation Of Poly(A) RNA

We collected the SEA/PHA induced splenocytes by centrifugation and washed them with cold PBS. In order to isolate total RNA from these induced splenocytes, we lysed the cells immediately with a solution of guanidinium thiocyanate (J. M. Chirgwin et al., "Isolation Of Biologically Active Ribonucleic Acid From Sources Enriched in Ribonuclease", *Biochemistry*, 18, pp. 5294–99 (1979)). We obtained an average of 30 mg total RNA per spleen. We then purified the RNA by precipitation out of a guanidinium hydrochloride solution and by chromatography on oligo(dT) cellulose (J. M. Chirgwin et al., supra). At this stage about 1 mg RNA (of which more than 60% is rRNA) remained.

We dissolved the resulting poly A+ RNA in sterile water, heated the mixture for 1 min at 68° C. and fractionated it on a 5–20% sucrose gradient in 10 mM Tris-HCl (pH 7.5), 1 mM EDTA, employing 1–2 mg RNA per gradient and 40,000 rpm for 16 h at 4° C. in a Beckman SW41 Ti rotor. We collected twenty-five fractions (0.4 ml each) in an ISCO gradient fractionator while measuring the optical density (254 nm) continuously.

We assessed the quality of the isolated RNA by measuring the height of the 5S and 18S rRNA peaks (28S rRNA was at the bottom of the tube) after centrifugation in a parallel gradient of approximately 300 µg oligo(dT) cellulose run through RNA.

We precipitated the RNA in each fraction for at least 2 h at −20° C., collected it by centrifugation (10,000 rpm, 30 min, −20° C., HB4 Sorvall rotor) and washed it with 70% ethanol. After the RNA was dried, we dissolved it in 25–50 µl sterile water.

We translated each of the poly A+ RNA sucrose gradient fractions in wheat germ extract (total vol 10 µl), in the presence of $^{35}$S-methionine (B. Roberts and B. M. Paterson, "Efficient Translation Of TMV RNA And Rabbit Globin 5S RNA In A Cell-Free System From Commercial Wheat Germ", *Proc. Natl. Acad. Sci. USA*, 70, pp. 2330–34 (1973)) and analyzed the synthesized proteins on a 12.5% SDS-polyacrylamide gel (U. K. Laemmli, "Cleavage Of Structural Proteins During Assembly Of The Head Of Bacteriophage T4", *Nature*, 227, pp. 680–85 (1970)). The synthesis of large polypeptides in this system demonstrated that the RNA fractions prepared by us contained RNA that was free of any inhibitors of in vitro translation.

Figure 2:
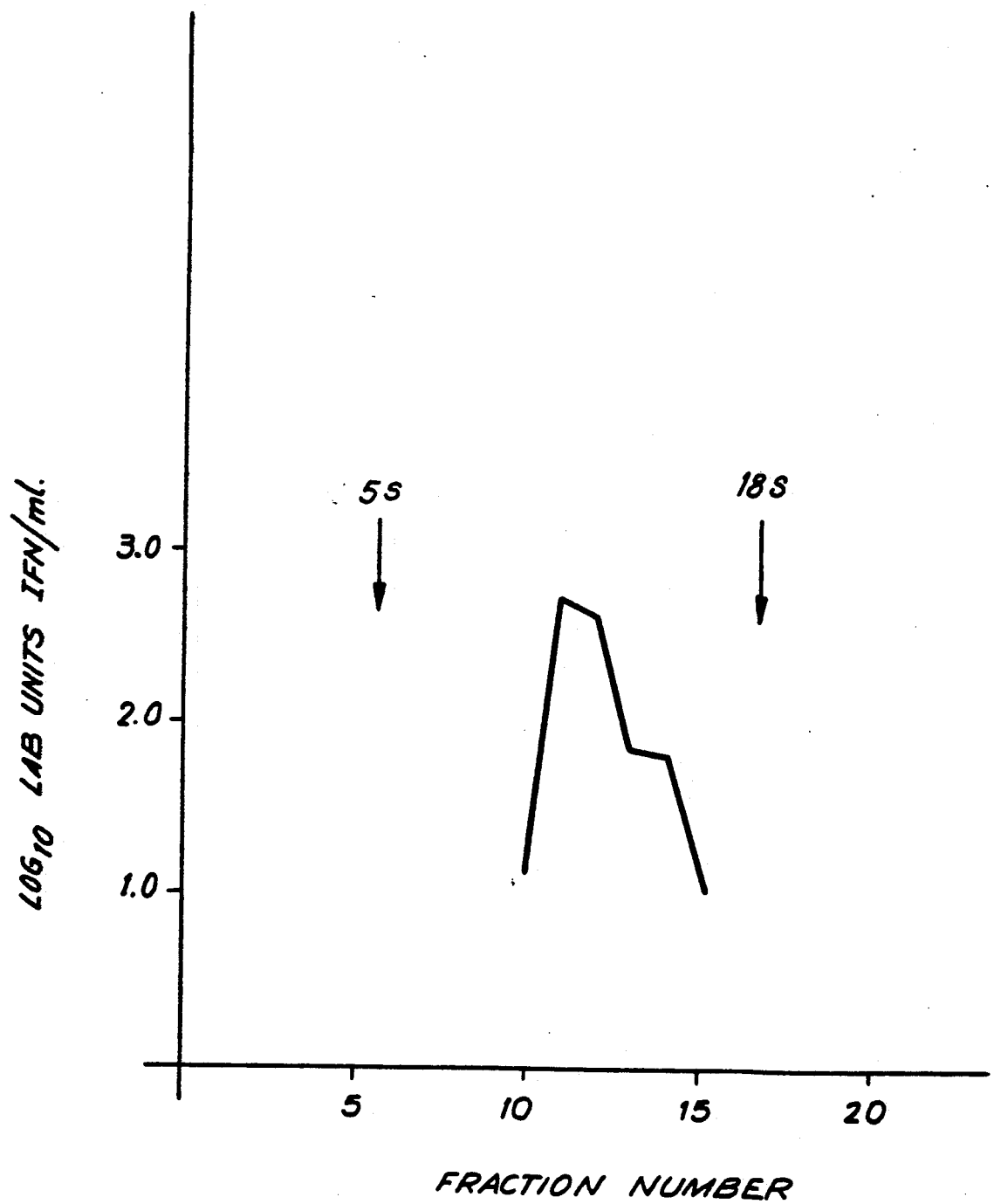
FIG. 2 is a graphical representation of the IFN encoding activity of a series of sucrose-gradient RNA fractions prepared in accordance with this invention.

We also assayed the poly A+ RNA fractions to determine the antiviral activity encoded by the mRNA. For this assay, we microinjected 50 nl of poly A+ RNA (1 mg/ml) into each of 15 to 20 *Xenopus laevis* oocytes and incubated the oocytes for 3 days at 20° C. We then withdrew the medium and stored the oocytes at −70° C. until we assayed, as before for the splenocyte medium, the secreted translation products for their antiviral activity (A. Colman and J. Morser, "Export Of Proteins From Oocytes Of *Xenopus Laevis*", *Cell*, 17, pp. 517–26 (1979)). We have depicted in FIG. 2 a graphical presentation of the results of our assay. These assays generally yielded an IFN activity which was 30 to 100 times lower than the antiviral activity of the splenocyte medium. Occassionally, the assays suggested evidence for heterogeneity of the IFN-specific RNA because there was sometimes a shoulder or even a faster moving active species.

For the IFN-active fractions, we also examined the antigenic properties of the IFN excreted by the oocytes by attempting to neutralize (1 h at 37° C.) the antiviral activity of that IFN with an excess of antiserum prepared against human IFN-β (a gift of Dr. E. De Clercq (anti-IFN-β serum (goat)) and antiserum prepared against human IFN-α (gifts of Dr. K. Cantell (anti-IFN-α (sheep)) and Dr. J. Vilcek (anti-IFN-α serum (rabbit)) and mixtures of them. We observed that the oocyte IFN samples were not neutralized by those antisera. However, the IFN activity of those samples was neutralized by antiserum prepared against IFN-γ (a gift of Dr. M. P. Langford and Dr. G. J. Stanton (rabbit) or prepared by us by immunizing mice (Balb/c) with partially purified IFN-γ obtained from our induced splenocytes).

In order to purify the IFN-γ specific mRNA further, we pooled the RNA from the active sucrose gradient fractions, dissolved it in a buffer, containing 50% formamide, 100 mM LiCl, 5 mM EDTA, 0.2% SDS, 10 mM Tris-HCl (pH 7.4) and heated it for 1 min at 50° C. We then centrifuged it on a 5–20% sucrose gradient (0.1 mg RNA/qradient), containing the above buffer, at 56,000 rpm for 5 h at 18° C. in a Beckman SW56 Ti rotor. Twenty fractions of 0.2 ml were collected and we precipitated the RNA from each fraction by allowing it to stand overnight at −20° C. with an equal vol 1M NaCl and 2.5 vol EtOH.

We assayed the RNA in each fraction as before in oocytes. In these assays the IFN activity appeared to be resolved into two peaks (11–13S and 15–16S). We were not able to determine whether the observed sedimentation heterogeniety is due to different steps in denaturation, to a different length of the poly A-tail or whether it represents two distinct IFN-mRNA species.

At this point it should be recognized that even the poly(A) RNA product obtained from the sucrose gradients contains a very large number of different mRNAs Except for the mRNA specific for IFN-γ, the other mRNAs are undesirable contaminants (FIG. 1). Unfortunately, these contaminant RNAs behave similarly to HuIFN-γ mRNA throughout the remainder of the cloning process of this invention. Therefore, their presence in the poly(A) RNA will result in the ultimate preparation of a large number of unwanted bacterial clones which contain genes that may code for polypeptides other than IFN-γ. This contamination presents complex screening problems in the isolation of the desired IFN-γ hybrid clones. In the case of IFN-γ, the screening problem is further exacerbated by the lack of a sufficiently purified sample of HuIFN-γ mRNA or DNA or portion thereof to act as a screening probe for the identification of the desired clones. Therefore, the screening process for the IFN-γ clones is very time-consuming and difficult. Further, because only a very small percentage of IFN-γ clones themselves are expected to express IFN-γ in a biologically or immunologically active form, the isolation of an active clone is a "needle in a haystack" screening process.

Advantageously, we may use recombinant DNA technology to provide a purified sample of HuIFN-γ mRNA or cDNA or a portion thereof. This purified mRNA or cDNA can then be used to screen rapidly very large numbers of bacterial clones and thereby markedly increase the probability of isolating a clone which expresses IFN-γ in an active form.

SYNTHESIS OF DOUBLE-STRANDED cDNA CONTAINING IFN-γ cDNA

Poly(A) RNA enriched in IFN-γ mRNA was used as a template to prepare complementary DNA ("cDNA"), essentially as described by R. Devos et al., "Construction And Characterization Of A Plasmid Containing A Nearly Full-Size DNA Copy Of Bacteriophage MS2 RNA", *J. Mol. Biol.*, 128, pp. 595–619 (1979), for the construction of a plasmid containing a DNA copy of bacteriophage MS2 RNA.

We incubated 40 μg poly A+ RNA (FIG. 2, pooled gradient fractions 11, 12, 13) for 30 min at 43° C. in a mixture of 100 μl 50 mM Tris HCl (pH 8.3) 30 mM β-mercaptoethanol, 50 mM KCl, 10 mM MgCl$_2$, 4 dNTPs 0.5 mM each, 10 pg pT$_{12-18}$, 100 μCi α-$^{32}$P dATP and 100 μCi α-$^{32}$P dCTP (2500 Ci/mole each), 4 mM Na$_4$P$_2$O$_7$ and 100 units AMV reverse transcriptase. We stopped the reaction with EDTA and after phenol extraction loaded the mixture onto a Sephadex-G75 column. We precipitated the nucleic acids in the void fractions with ethanol overnight at −20° C. and removed them by centrifugation. We washed the pellet with 70% ethanol, dried it and took it up in 40 μl H$_2$O.

The cDNA population synthesized above is in fact a complex mixture of cDNAs originating from the different mRNAs which were present in the enriched poly A+ mRNA (FIG. 1). In addition, because of premature termination by AMV reverse transcriptase, many of the cDNAs are incomplete copies of the various mRNAs in the poly A RNA (not shown in FIG. 1).

Before rendering the cDNA double-stranded, it was removed from its association to the complementary template mRNA by heating the above-described water mixture at 100° C. for 30 sec and then immediately chilled at 0° C. We added 3 pg pancreatic RNase and 3 units T$_1$-RNase and incubated the mixture for 30 min at 37° C.

The cDNA strand was rendered double-stranded by adjusting the mixture to 100 μl by addition of a mixture of K-phosphate (pH 6.9) (final concentration 100 mM), dithiothreitol (4 mM), MgCl$_2$ (10 mM), 4 dNTPs (250 μM each), 50 μCi α-$^{32}$P dATP and 50 μCi α-$^{32}$P dCTP (2500 Ci/mole each), adding *E. coli* DNA polymerase I (Biolabs, 100 units) and incubating the resulting mixture for 3 h at 15° C. The reaction was stopped with EDTA, the mixture phenolized, passed over a Sephadex-G75 column and the void fractions precipitated as before with ethanol at −20° C. overnight.

To open the single-stranded hairpin loop which remains on the double-stranded cDNA structure, we removed the DNA by centrifugation, dried the pellet and took it up again in HzO and incubated the mixture for 30 min at 37° C. in 100 μl of 0.2M NaCl, 50 mM NaOAc (pH 4.5), 1 mM $ZnCl_2$ and 10 units of SI nuclease (Sigma). We stopped the reaction by extracting the mixture with phenol/$CHCl_3$/isoamylalcohol and precipitating the DNA for 2 h at −20° C. and 10 min at −70° C. by addition of 200 μl 2M $NH_4OAc$, 10 μg *E. coli* tRNA and 1 ml ethanol. We removed the pellet by centrifugation and dried it. This mixture of double-stranded cDNAs is heterogeneous both as a consequence of the heterogeneity of the poly A RNA employed as a template to prepare it (FIG. 1) and because of the probable premature termination of the cDNA transcripts by AMV transcriptase (not shown in FIG. 1).

To lessen the effect of the latter heterogeneity, we sized the double-stranded cDNA mixture by taking the pellet up in 20 μl 10 mM Tris-HCl (pH 7.5), 1 mM EDTA, incubating it for 5 min at 55° C., adding bromophenol blue-xylenecyanol FF and sucrose and electrophoresing the DNA overnight in a 4% polyacrylamide gel (Tris-borate, 20 cm×40 cm×0.3 cm, 200 V-20 mA); a 5'-$^{32}$P-labeled HaeIII digest of phage φX174 DNA being electrophoresed in a parallel lane as a marker. After autoradiography of the gel, we separated the DNA into fractions according to its position on the gel—g4 (800–1000 bp), g3 (1000–1250 bp) and g2 (1250–1400 bp). We cut out the gel slices corresponding to each fraction and eluted them overnight with 2 ml 0.5 M $NH_4OAc$, 10 mM $MgCl_2$, 0.1% SDS and precipitated the DNA with 2 vol ethanol (at −20° C.). After centrifugation, we took each pellet up in 100 μl $H_2O$ and incubated it for 10 min at 37° C. in the presence of 900 μl 10 mM Na-phosphate (pH 7.4) and 100 μl (packed vol) hydroxylapatite (Biorad). We then loaded the hydroxylapatite on a Sephadex-G75 column and after washing the column extensively with 2 mM Na-phosphate (pH 7.4), we eluted the DNA with 0.45M Na-phosphate (pH 7.4) and precipitated it with 1/10 vol 2M NaOAC (pH 5) and 2 vol ethanol.

Again it must be recognized that within each of our cDNA fractions is a large number of cDNAs, only a very few of which are IFN-γ-related cDNA (FIG. 1).

CLONING OF DOUBLE-STRANDED cDNA

A wide variety of host/cloning vehicle combinations may be employed in cloning or expressing the double-stranded cDNA prepared in accordance with this invention. For example, useful cloning or expression vehicles may consist of segments of chromosomal, non-chromosomal and synthetic DNA sequences, such as various known derivatives of SV40 and known bacterial plasmids, e.g., plasmids from *E. coli* including col E1, pCR1, pBR322, pMB9 and their derivatives, wider host range plasmids, e.g., RP4, phage DNAs, e.g., the numerous derivatives of phage λ, e.g., NM989, and other DNA phages, e.g., M13 and filamentous single-stranded DNA phages and vectors derived from combinations of plasmids and phage DNAs such as plasmids which have been modified to employ phage DNA or other expression control sequences or yeast plasmids such as the 2μ plasmid or derivatives thereof. Useful cloning or expression hosts may include bacterial hosts such as *E. coli* HB101, *E. coli* X1776, *E. coli* X2282, *E. coli* MCRI and strains of Pseudomonas, *Bacillus subtilis*, *Bacillus stearothermophilus* and other bacilli, yeasts and other fungi, animal or plant hosts such as animal (including human) or plant cells in culture or other hosts. Of course, not all host/vector combinations may be equally efficient. The particular selection of host/cloning vehicle combination may be made by those of skill in the art after due consideration of the principles set forth without departing from the scope of this invention.

Furthermore, within each specific cloning or expression vehicle, various sites may be selected for insertion of the double-stranded DNA. These sites are usually designated by the restriction endonuclease which cuts them. These sites are well recognized by those of skill in the art. It is, of course, to be understood that a cloning or expression vehicle useful in this invention need not have a restriction endonuclease site for insertion of the chosen DNA fragment. Instead, the vehicle could be joined to the fragment by alternative means.

The vector or cloning or expression vehicle, and in particular the site chosen therein for attachment of a selected DNA fragment to form a recombinant DNA molecule, is determined by a variety of factors, e.g., number of sites susceptible to a particular restriction enzyme, size of the protein to be expressed, susceptibility of the desired protein to proteolytic degradation by host cell enzymes, contamination or binding of the protein to be expressed by host cell proteins difficult to remove during purification, expression characteristics, such as the location of start and stop codons relative to the vector sequences, and other factors recognized by those of skill in the art. The choice of a vector and an insertion site for a particular gene is determined by a balance of these factors, not all selections being equally effective for a given case.

Although several methods are known in the art for inserting foreign DNA into a cloning vehicle or expression vector to form a recombinant DNA molecule, the method preferred for initial cloning in accordance with this invention is digesting pSV529 DNA (infra) with BamHI, filling in the BamHI site and adding dC tails to the 3' termini by terminal transferase. The double-stranded cDNA is then ligated to the pSV529 DNA after first tailing it with dG tails. The tailed-DNA and tailed-cDNA may then be annealed to insert the DNA in the chosen site of the plasmid and to recircularize the hybrid DNA, the complementary character of the dG-dC tails permitting their cohesion and reconstruction of a BamHI site (FIG. 1). The resulting recombinant DNA molecule now carries an inserted gene at the chosen position in the cloning vector (FIG. 1).

Of course, other known methods of inserting DNA sequences into cloning or expression vehicles to form recombinant DNA molecules are equally useful in this invention. These include, for example, dA-dT tailing, direct ligation, synthetic linkers, exonuclease and polymerase-linked repair reactions followed by ligation, or extension of the DNA strand with DNA polymerase and an appropriate single-stranded template followed by ligation.

It should, of course, be understood that the nucleotide sequences or cDNA fragments inserted at the selected site of the cloning vehicle may include nucleotides which are not part of the actual structural gene for the desired polypeptide or may include only a fragment of the complete structural gene for the desired protein.

It is only required that whatever DNA sequence is finally inserted, a transformed host will produce a polypeptide having a biological or immunological activity of HuIFN-γ or that the DNA sequence itself is of use as a hybridization probe to select clones which contain DNA sequences useful in the production of polypeptides having an immunological or biological activity of HuIFN-γ.

The cloning vehicle or expression vector containing the foreign gene is employed to transform a host so as to permit that host to express polypeptides displaying an immunological or biological activity of HuIFN-γ for which the hybrid gene codes. The selection of an appropriate host is also controlled by a number of factors recognized by the art. These include, for example, compatibility with the chosen vector, toxicity of proteins encoded by the hybrid plasmid, ease of recovery of the desired protein, expression characteristics, bio-safety and cost. A balance of these factors must be struck with the understanding that not all hosts may be equally effective for either the cloning or expression of a particular recombinant DNA molecule.

In the present synthesis, the preferred initial cloning vehicle is pSV529 and the preferred initial restriction endonuclease site is BamHI. The preferred initial host is E. coli DH1 (λ).

(a) Preparation Of BamHI-Cleaved, dC-Tailed pSV529 DNA pSV529 is an chimaeric SV40 plasmid expression vector from which a substantial amount of the late region has been removed. The construction lacks most of the VP1 gene (between 0.945 and 0.145 map units), but retains all the regions which are implicated in replication, initiation and termination of transcription and in splicing and polyadenylation of 16S and 19S mRNA. pSV529 is designed to express a gene under late SV40 transcriptional control.

Figure 3:
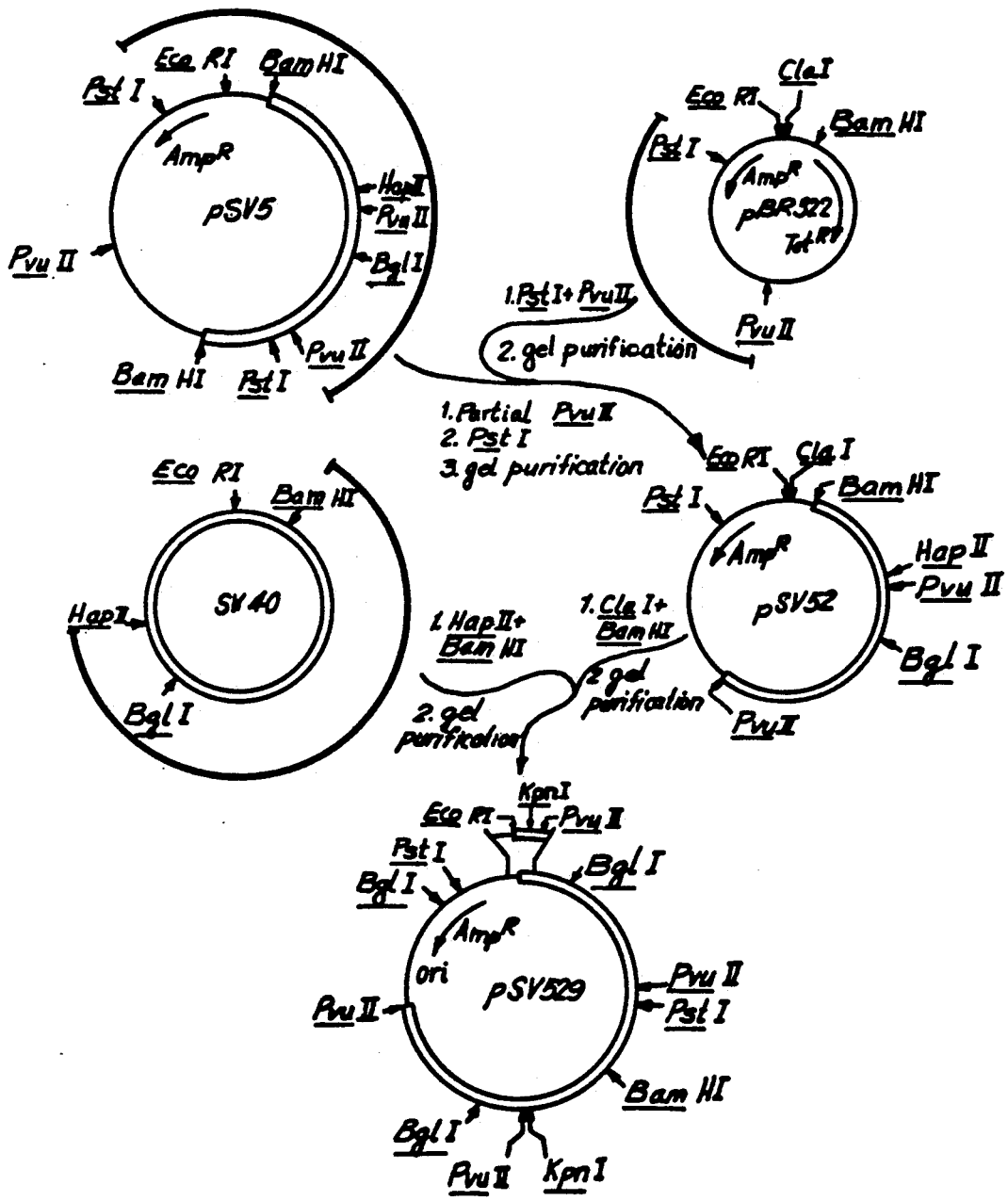
FIG. 3 is a schematic outline of the construction of pSV529.

The construction of pSV529 is depicted in FIG. 3. Chimaeric plasmid pSV5 (a gift of Dr. C. J. Lai) consists of pBR322 having SV40 DNA information inserted at the BamHI site. The SV DNA in pSV5 extends from position 0.945 (a HindIII site now converted to a BamHI site) anti-clockwise as far as the unique SV40 BamHI site (position 0.145).

We partially digested supercoiled plasmid pSV5 DNA with PvuII in the presence of ethidium bromide and after phenolization and precipitation, we further digested it with PstI and purified the 4330 bp long donor DNA fragment of pSV5 on a gel. We then completely digested 5 pg pBR322 DNA with PvuII and PstI and purified the 1542 bp long pBR322 PstI-PvuII acceptor fragment on a gel (FIG. 3). We mixed the two purified fragments (donor and acceptor) together in equimolar ratio and ligated them with T4 ligase at 16° C. We use 1/5 of the ligation mixture to transform E. coli K12 strain HB101 and thereby obtained more than 600 putative pBR322-SV40 recombinants. One of these clones, pSV52, yielded the expected PvuII fragments upon restriction analysis. It was also characterized by HindII and HindIII digestion and had a unique BamHI site (FIG. 3).

We next digested pSV52 with ClaI and BamHI and recovered the resulting 5520 bp long fragment from low melting point agarose. We also digested SV40 DNA with BamHI and HapII and recovered a BamHIHapII fragment of 3096 base pairs that spans the early region of the SV40 genome (map units 0.145 to 0.725). Although the ClaI (ATCGAT) and the HapII (CCGG) endonuclease recognition sites differ, the cohesive ends (CG) generated by these endonucleases are identical. Accordingly, the 5520 bp long ClaIBamHI could be ligated to the gel-purified 3096 bp long HapII-BamHI fragment (FIG. 3).

After transformation of E. coli K12 (strain HB101), we obtained more than 500 carbenicillin resistant clones. Six of the eight recombinant clones, which we analyzed on agarose gel, were found to yield the desired fragments upon digestion with PvuII, namely a 2341 bp, a 2263 bp and two molar equivalents of a 2006 bp fragment. This is consistent with the expected repetition of a 2080 bp SV40 fragment from (PvuII (0.33) to HapII (0.725)) spanning the 5'-proximal half of the large T-antigen gene and the origin sequence of SV40.

Figure 4:
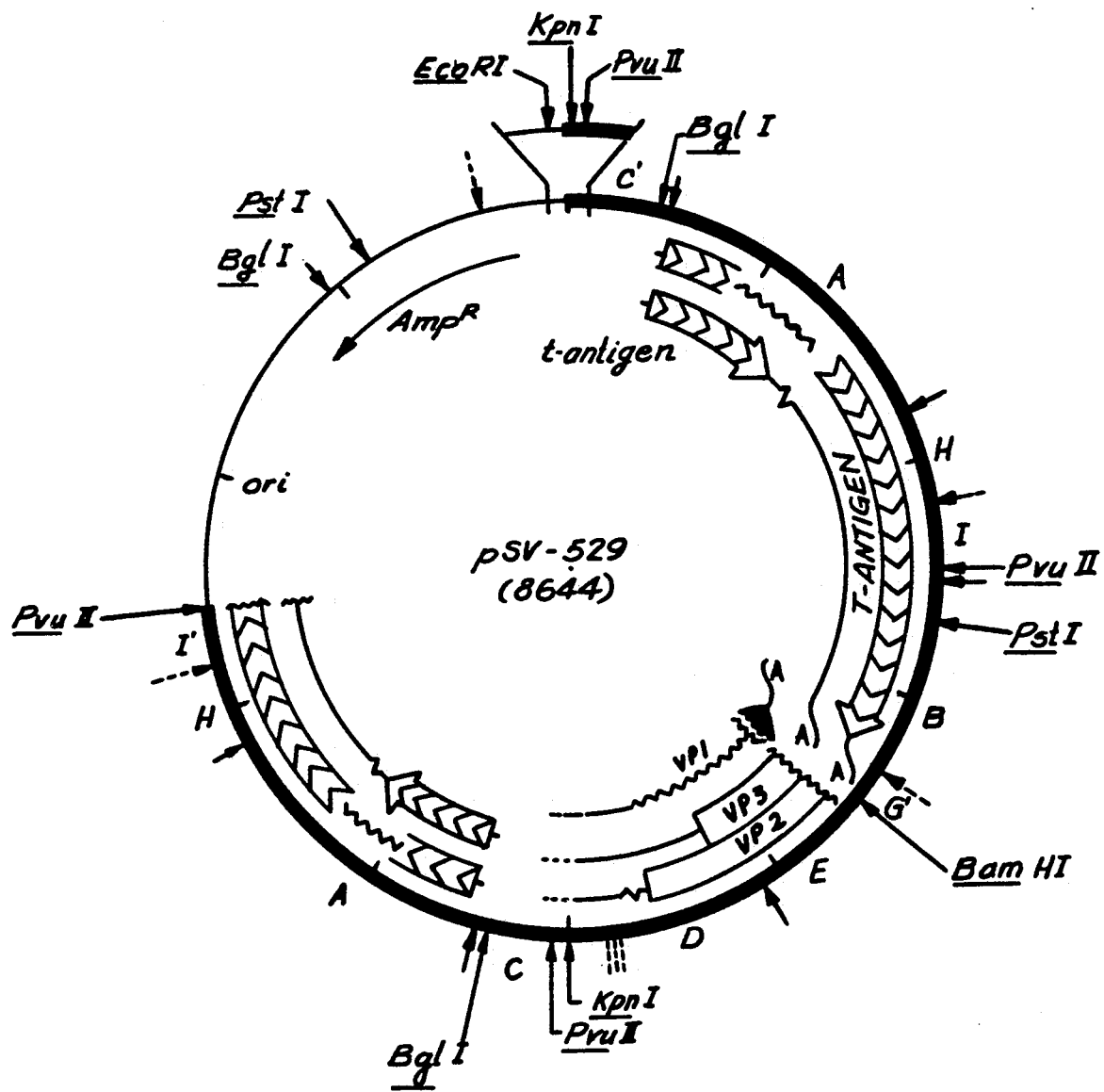
FIG. 4 is a pictorial representation of pSV529.

We selected one of these recombinant plasmids and designated it pSV529 (FIGS. 3 and 4). The main features of pSV529 are: (a) the complete early region of the SV40 genome is present and codes for small-t and large-T antigens as well as the region required for replication in monkey cells, also present are the "enhancer" sequences located towards the late region of ori; (b) the gene for the major structural protein VP1 has been deleted (the HindIIIBamHI fragment from 0.945–0.145 map units); (c) a unique BamHI-site is present on the chimaeric plasmid into which foreign sequences can be inserted for expression under the control of the SV40 late promotor, this BamHI-site is present 39 nucleotides after the late 16S mRNA acceptor splice site and 12 nucleotides before the (now removed) initiation codon of the VP1 gene; (d) donor and acceptor splice sites for the major 16S late message are present; (e) a polyadenylation site from the SV40 late region is present (SV40 map units 0.17); and (f) duplication of a 2080 bp segment of SV40 DNA (between map position 0.33 and 0.725) enables homologous recombination in monkey cells and generates an SV40 replicon from which the plasmid sequences have been deleted but which now contains the inserted gene instead of the viral structural gene VP1.

We digested 50 μg pSV529 DNA with 40 units BamHI restriction enzyme for 2 h at 37° C. in 60 μl 8 mM MgCl$_2$, 40 mM NaCl, 100 mM Tris-HCl (pH 7.4). We stopped the reaction with EDTA and the mixture was phenolized (3x), ether extracted (2x) and precipitated with 1/10 vol 2 M KOAc (pH 5) and 2 vol ethanol.

We then separated the precipitated, linearized (BamHI) pSV529 DNA and washed it (2x) with 70% ethanol, dried it, took it up in H$_2$O and incubated it for 30 min at 37° C. in 50 μl of a mixture of 50 mM Tris-HCl (pH 8.3), 50 mM KCl, 10 mM MgCl$_2$. 30 mM β-mercaptoethanol, 4 dNTPs at 250 μM each and 50 units AMV reverse transcriptase. We stopped the reaction with EDTA and extracted the mixture with phenol/CHCl$_3$/isoamyl alcohol. The buffer and mixture were loaded on a Sephadex-G75 column (20 cm × 0.5 cm) in 10 mM Tris-HCl (pH 7.5), 1 mM EDTA and the void fractions precipitated with 2M KOAc (pH 5) and ethanol at −20° C. for 1 h.

We separated the DNA by centrifugation, dried it and took it up in 30 μl 10 mM Tris-HCl (pH 7.5), 1 mM EDTA, heated it for 30 sec at 68° C. and chilled it on ice. We then incubated the DNA at 37° C. in 200 μl of a mixture of 0.14M K-cacodylate, 30 mM Tris buffer (pH 6.8), 1 mM CoSO$_4$, 1 mM dithiothreitol, 0.1 mM dCTP, 100 μCI α-$^{32}$P dCTP (2500 Ci/mole) and 100 units terminal deoxynucleotidyl transferase (P-L Biochemicals). After 5 min and 10 min, we withdrew aliquots of 100 μl and stopped the reaction with EDTA.

We extracted the aliquots with phenol/CHCl₃/isoamyl alcohol and purified the DNA by chromatography through a Sephadex-G75 column as above. The DNA in the void fractions was precipitated with ethanol, centrifuged, dried and taken up in 50 μl 10 mM Tris-HCl (pH 7.5), 1 mM EDTA. It was calculated that an average of 22 and 36 dCMP residues were added at the 3'-ends of linearized pSV529 DNA after 5 min and 10 min incubation, respectively. Moreover, there was little internal tailing as indicated by agarose gel electrophoresis of the PvuII digested dC-tailed pSV529 DNA.

(b) Preparation Of dG-Tailed cDNA Derived From Induced Splenocytes

The double-stranded cDNA (fractions g2, g3 and g4), described above was centrifuged, dried, taken up in 20 μl 10 mM Tris-HCl (pH 7.5), 1 mM EDTA and incubated for 10 min at 37° C. in 30 μl of a mixture containing 0.14M K-cacodylate, 30 mM Tris buffer (pH 6.8), 1 mM CoSO₄, 1 mM dithiothreitol, 0.2 mM ³H-dCTP (5.7 Ci/mmole, 1.54 ml/mCi) and 20 units terminal desoxynucleotidyl transferase. We stopped the reaction with EDTA.

We then extracted the reaction mixture with phenol/CHCl₃/isoamyl alcohol and passed it over a Sephadex-G75 column. We precipitated the DNA in the void fractions overnight with KOAc and ethanol and removed the DNA by centrifugation. We dried the recovered DNA and took it up in 30 μl of a mixture 10 mM Tris-HCl (pH 7.5), 1 mM EDTA, 0.1M NaCl. It was calculated that an average of 50 dGMP residues were added at the 3'-ends of the dsDNA (each of fractions g2, g3 and g4) (60 ng, approximately 0.1 pmoles each).

(c) Annealing of dC-elongated pSV529 and dG-elongated cDNA

We mixed 15μl dG-tailed ds DNA (0.05 pmoles) from each of fractions g2, g3 and g4 with 2 μl (0.15 pmoles) pSV529 linearized with BamHI filled in and dC-tailed. After 10 min 185 μl 10 mM Tris-HCl (pH 7.5), 1 mM EDTA, 0.1 M NaCl was added and we incubated the mixture for 5 min at 68° C., 2 h at 43° C. and slowly cooled it (4 h) to room temperature (25° C.).

The hybrid DNA obtained after annealing is, of course, a large mixture of different recombinant DNA molecules and some cloning vehicles without inserted DNA sequences. However, each recombinant DNA molecule contains a cDNA segment at the BamHI site. Each such cDNA segment may comprise a gene or a fragment thereof. Only a very few of the cDNA fragments code for HuIFN-γ or a portion thereof (FIG. 1). The vast majority code for one of the other proteins or portions thereof whose mRNAs were part of the poly(A) RNA used in the process of this invention (FIG. 1). It should also be understood that none of the clones of the above-prepared library may permit the expression of polypeptides displaying an immunological or biological activity of IFN-γ. Instead, they may only be useful in screening for such a clone.

(d) Transfection of E. coli DH1 (γ) With The Annealed HYbrid DNA

Appropriate containment facilities were employed as necessary for the transfection process and for all subsequent steps in which the resulting transformants were handled.

We added 33 μl of the mixture of annealed DNA (for each of fractions g2, g3 and g4) to each of 100 μl competent E. coli DH1 (λ) cells. After standing at 0° C. for 30 min, the cells were incubated for 5 min at 41° C., 1 ml LB-medium was added and the mixture was further incubated at 37° C. for 45 min. We then plated ⅓ of each mixture (~350 μl) onto an agar plate containing 100 μg/μl carbenicillin and incubated the plates overnight at 37° C.

Since plasmid pSV529 includes the gene for penicillin resistance, E. coli hosts which have been transformed with a plasmid having that gene intact will grow in cultures containing that antibiotic to the exclusion of those bacteria not so transformed. Therefore, growth in carbenicillin-containing culture permits selection of hosts transformed with a recombinant DNA molecule or recyclized vector.

We picked individual colonies and grew them overnight in 200 μl LB-medium (containing carbenicillin) in microtiter plates. After adding dimethylsulphoxide to a final concentration of 10%, the plates were stored at −20° C.

The carbenicillin-resistant clones of each fraction (g4, g3 and g2) contain a variety of recombinant DNA molecules representing sized, complete or partial copies of the mixture of mRNAs in the poly A RNA obtained from the induced splenocytes (FIG. 1). The majority of these clones will contain a single recombinant DNA molecule. However, only a very few of these recombinant DNA molecules are related to HuIFN-γ. Accordingly, the clones must be screened to select the HuIFN-γ-related clones from the others.

SCREENING FOR A CLONE CONTAINING HuIFN-γ cDNA

There are several approaches to screen for bacterial clones containing HuIFN-γ cDNA. These include, for example, RNA selection hybridization (Alwine et al., infra), differential hybridization (T. P. St. John and R. W. Davis, "Isolation Of Galactose-Inducible DNA Sequences From Saccharomyces Cerevisiae By Differential Plaque Filter Hybridization", *Cell*, 16, pp. 443–52 (1979)); hybridization with a synthetic probe (B. Noyes et al., "Detection And Partial Sequence Analysis Of Gastrin mRNA By Using An Oligodeoxynucleotide Probe", *Proc. Natl. Acad. Sci. USA*, 76, pp. 1770–74 (1979)) or screening for clones that produce the desired protein by immunological (L. Villa-Komaroff et al., "A Bacterial Clone Synthesizing Proinsulin", *Proc. Natl. Acad. Sci. USA*, 75, pp. 3727–31 (1978)) or biological (A. C. Y. Chang et al., "Phenotypic Expression In E. coli Of A DNA Sequence Coding For Mouse Dihydrofolate Reductase", *Nature*, 275, pp. 617–24 (1978)) assays. We have chosen RNA selection hybridization as being the most convenient and promising method for primary clone screening.

A. RNA Selection Hybridization Assay

1. Overview Of The Initial Assay

Figure 5:
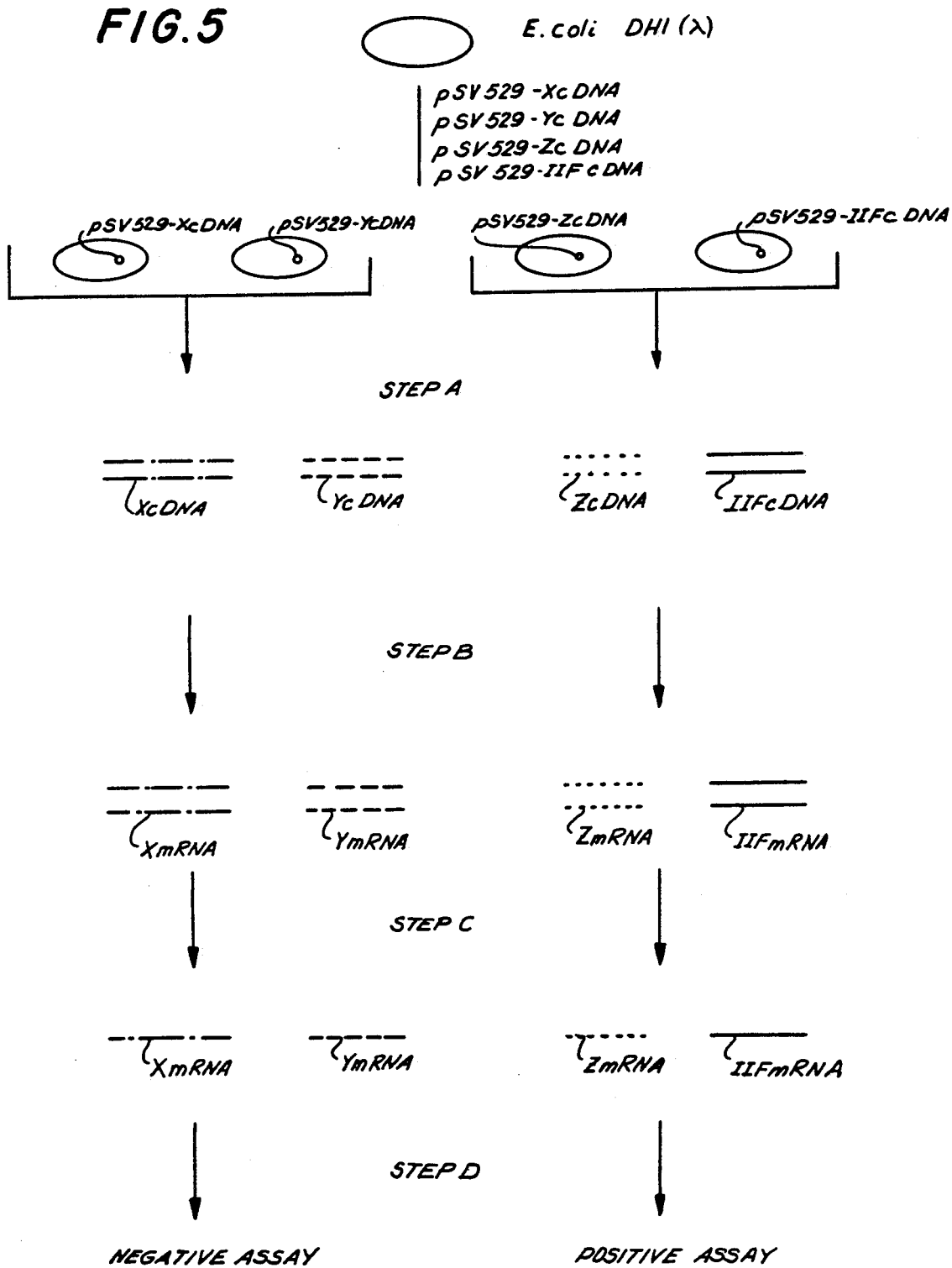
FIG. 5 is a schematic representation of the RNA selection hybridization assay employed in this invention.

Referring now to FIG. 5, the recombinant DNA molecules were isolated from pooled cultures of about 50 clones sensitive to carbenicillin from the above library of clones (two mixtures of 2 clones shown in FIG. 5) (Step A). The recombinant DNA molecules were cleaved (BamHI) and their inserts purified and hybridized to total RNA containing HuIFN-γ mRNA prepared as before (Step B). All DNA-insert-total RNA hybrids were separated from the non-hybridized total RNA and the hybridized total RNA was recovered from the hybrids (Step C). The recovered RNA was assayed for HuIFN-γ mRNA activity as above (Step D). If, and only if, the mixture of recombinant DNA molecules contains a recombinant DNA molecule having a BamHI inserted nucleotide sequence capable of hybridizing to the HuIFN-γ mRNA in the total RNA, under stringent hybridization conditions, will the mRNA released from that hybrid cause the formation of HuIFN-γ in oocytes, because mRNA released from any other recombinant DNA molecule-total RNA hybrid will not be IFN-γ-related.

If a group of 50 clones gave a positive response, the clones were regrouped into 6 subgroups (4 subgroups of 8 and 2 subgroups of 9) and each subgroup assayed as before. This process was continued until a single clone responding to this assay was identified.

There is no assurance that the recombinant DNA molecules and bacterial cultures transformed therewith, which are thus identified, contain the complete IFN-γ cDNA sequence or even that the DNA sequence actually codes for IFN-γ or will permit the clone to express polypeptides displaying an immunological or biological activity of IFN-γ. However, the recombinant DNA molecules will certainly contain extensive nucleotide sequences complementary to the IFN-γ mRNA coding sequence. Therefore, the recombinant DNA molecule may at least be used as a source of a probe to screen rapidly other recombinant DNA molecules and clones transformed with them to identify further sets of clones which may contain an authentic or complete IFN-γ nucleotide coding sequence. These clones may then be analyzed for possible expression of polypeptides displaying a biological or immunological activity of IFN-γ. And, the nucleotide sequence of the inserted DNA fragment of these hybrid plasmids and its amino acid translation product may be determined and employed to improve the yield and activity of IFN-γ.

2. Execution Of The Initial Assay

Step A—Purification Of "Insert-DNA" And Preparation Of Nitrocellulose Filters Containing That "Insert-DNA"

We divided each of the above-prepared libraries (g2, g3 and g4) into groups of 50 clones and grew each set of 50 overnight on a single agar plate. We then suspended the bacteria derived from these clones in 5 ml LB-medium, inoculated 0.5 l LB-medium with this suspension, grew the bacteria suspension overnight (without amplification of the plasmids). We isolated the DNA from these cultures by lysozyme-Triton X 100 lysis, polyethylene glycol precipitation of the cleared lysate and CsCl gradient centrifugation in the presence of ethidium bromide. We then took up the supercoiled DNA of each mixture of 50 clones (~250 μg) in 200 μl 10 mM Tris-HCl (pH 7.5), 1 mM EDTA and digested 150 μl of this solution with BamHI to excise the "DNA-insert". After cleaving of the DNA was complete (checked by electrophoresis of 5 μl in a 4% polyacrylamide gel), we phenolized the DNA mixture, extracted it with ether and precipitated the DNA, as before, with ethanol.

After centrifugation and extensive drying, the DNA pellet was taken up in 200 μl 10 mM Tris-HCl (pH 7.5), 1 mM EDTA, heated for 5 min at 68° C., chilled and loaded on an 11-ml 5–20% sucrose-gradient in 10 mM Tris-HCl (pH 7.5), 1 mM EDTA. We centrifuged this gradient for 16 h in a Beckman SW41 rotor at 40K, 4° C.

We then fractionated the gradients and the fraction containing the mixture of excised "insert-DNA" (~20 μg) was precipitated with 1/10 vol 2M KOAc (pH 5) and 2 vol ethanol at −20° C. for at least 3 h.

We centrifuged the precipitated mixture to separate the "insert-DNA" and then took up the pellet in a total of 160 μl 10 mM Tris-HCl (pH 7.5), 1 mM EDTA (10 μl was used for electrophoresis on a 4% polyacrylamide gel), heated the mixture for 5 min at 100° C. and added 150 μl 1M NaOH. We then neutralized the mixture by addition of 900 μl of a mixture containing 1.5M NaCl, 0.15M Na-citrate, 0.25M Tris-HCl (pH 8.0), 0.25M HCl and slowly filtered it through a nitrocellulose filter (7 mm φ, millipore HAWP 0.45μ) to adsorb the "insert-DNA" to the filter. The filters were air-dried, washed with 0.9M NaCl, 0.09M Na-citrate, dried and baked under vacuum for 2 h at 80° C.

Step B—Hybridization Of The Insert-DNA With Total RNA

We prepared 500 μl of a mixture of 65% formamide (deionized with Amberlite MB1, Serva), 0.2 SDS, 20 mM HEPES (pH 6.4), 0.4M NaCl and poly A RNA (50 to 100 μg, derived from SEA-induced splenocytes and purified on a 5–20% sucrose gradient, as described previously). The mixture was heated for 1 min at 65° C. in a siliconized Eppendorf tube. We then added this mixture to a 15 ml Corex tube containing 20 halved nitrocellulose filters (marked with a pencil and moistened with 0.9M NaCl, 0.09M Na-citrate). These 20 nitrocellulose filters represented 20 groups of 50 clones each prepared from a part of the g3 clone library. We incubated the filters in this mixture for 2 h at 50° C.

Step C—Separation Of Hybridized Total RNA-Insert-DNA From Non-Hybridized Total RNA We transferred the 20 filters now containing the hybridized total RNA-Insert-DNA to a 50 ml plastic tube and washed them 9 times with 50 ml of a solution of 10 mM Tris-HCl (pH 7.6), 0.15M NaCl, 1 mM EDTA, 0.5% SDS and 2 times with the above buffer without SDS at 65° C. Each individual filter was then transferred to a siliconized Eppendorf tube containing 150 μl H₂O and 2 μl (4 ug) poly A⁻ RNA (oligo (dT)cellulose run-through RNA of splenocytes). We heated the tubes for 1 min at 100° C. and immediately froze them in a CO₂/ethanol bath. After thawing the tubes to room temperature, we removed the filter from the tube and precipated the eluted RNA overnight at −20° C. with 20 μl 2M NaOAc (pH 5) and 400 μl ethanol. We collected the RNA by centrifugation, washed the pellet (2x) with 70% ethanol and dried it.

Step D—Determination Of IFN-γ mRNA Activity

Each of the 20 RNA pellets, corresponding to the 20 filters and therefore the 20 original groups of 50 clones from fraction g3, was taken up in 2 μl H₂O and the RNA injected into each of 15 to 20 *Xenopus laevis* oocytes as before. After 3 days at 23° C., the oocyte medium was removed and assayed as before for IFN antiviral activity.

3. Results Of The RNA Selection Hybridization Assay

Of the 20 groups of 50 clones from cDNA fraction g3 (1000–1250 bp), groups 1, 2, 3, 10, 15 and 18 contained "insert-DNA" that hybridized to mRNA (from poly(A) RNA of induced splenocytes) that encoded IFN activity as measured in oocytes in the initial assays. After a second hybridization and assay, as described above, groups 1, 2 and 15 continued to be positive.

We divided the 50 clones of group 2 into 6 subgroups, subgroups 2-1 through 2-6, respectively (4 groups of 8 clones and 2 groups of 9 clones), and repeated the above described hybridization and assay procedures on nitrocellulose filters containing insert-DNA from those 6 subgroups. After this hybridization subgroups 2-2 and 2-6 displayed interferon activity in an initial assay. In a second screening of subgroups 2-1 to 2-6, subgroup 2-6 continued to display a strong IFN antiviral activity.

We therefore divided subgroup 2-6 into its individual 8 clones (designated 2-6.1 through 2-6.8) and repeated the binding of insert-DNA to nitrocellulose filters, RNA hybridization and assay, as described above, for the 5 of those 8 clones that had insert DNA able to be excised, as described above, with BamHI. After this procedure clones 2-6.2, 2-6.3 and 2-6.7 were positive in the interferon assay. A second hybridization also demonstrated that these clones contained insert DNA capable of binding mRNA that encoded IFN activity.

Since restriction analysis demonstrated that the insert DNAs excised from clones 2-6.2, 2-6.3 and 2-6.7 was identical, we treated the 3 clones as one and designated it as *E. coli* DH1 ($\lambda$) (pSV529 (BamHI)/HIIF-0, its recombinant DNA molecule pSV529(BamHI/HIIF-0, "pHIIF-SV-$\gamma_0$" and its insert DNA $\gamma_0$). This nomenclature indicates that the clone and recombinant DNA molecule comprises plasmid pSV529 containing at the BamHI site HuIFN-$\gamma$-related cDNA ("HIIF" or "$\gamma$"), the particular molecule being the first identified ("0,""$\gamma_0$").

IDENTIFICATION OF CLONES CONTAINING RECOMBINANT DNA MOLECULES CROSSHYBRIDIZING TO $\gamma_0$ pHIIF-SV-$\gamma_0$, isolated as described above, was used to screen the library of clones previously prepared from cDNA of groups g3 (1000–1250 bp) and g2 (1250–1400 bp) by colony hybridization (M. Grunstein and D. S. Hogness, "A Method For The Isolation Of Cloned DNA's That Contain A Specific Gene", *Proc. Natl. Acad. Sci. USA*, 72, pp. 3961–65 (1975)). This method allows rapid identification of related clones by hybridization of a radioactive probe made from pHIIF-SV-$\gamma_0$ to the DNA of lysed bacterial colonies fixed in nitrocellulose filters.

The library of clones stored in microtiter plates, as described above, was replicated on similar size nitrocellulose sheets (0.45 $\mu$m pore diameter, Schleicher and Schuel or Millipore), which had been previously boiled to remove detergent, and the sheets placed on LB-agar plates, containing carbenicillin (100 $\mu$g/$\mu$l ). Bacterial colonies were grown overnight at 37° C. Lysis and fixation of the bacteria on the nitrocellulose sheets took place by washing consecutively in 0.5N NaOH (twice for about 7 min), 1M Tris-HCl (pH 7.5) (about 7 min), 0.5M Tris-HCl (pH 7.5) and 1.5M NaCl (about 7 min), 2 x SSC (0.15M NaCl, 0.015M sodium citrate (pH 7.2) (about 7 min)). After thorough rinsing with ethanol and air drying, the sheets were baked at 80° C. for 2 h in vacuo and stored at room temperature.

A DdeI restriction fragment specific for the insert DNA $\gamma_0$ fragment (infra) served as the probe for colony hybridization. This fragment (~620 base pairs) was purified by electrophoresis of the DdeI digestion products of pHIIF-SV-$\gamma_0$ in a 4% polyacrylamide gel. After staining the DNA bands with ethidium bromide, the specific fragment was eluted and any residual ethidium bromide was removed by isoamyl alcohol extraction. The specific fragment was then concentrated by precipitation with ethanol and $^{32}$P-labelled by "nick translation" (P. W. J. Rigby et al., "Labeling Deoxyribonucleic Acid To High Specific Activity In Vitro By Nick Translation With DNA Polymerase I", *J. Mol. Biol.*, 113, pp. 237–51 (1977)) by incubation in 50 $\mu$l 50 mM Tris-HCl (pH 7.), 10 mM MgCl$_2$, 20 mM $\beta$-mercaptoethanol, containing 2.5 $\mu$l each of dCTP, dTTP and dGTP at 400 $\mu$M, 100 pmoles $\alpha$-ATP (Amersham, 2000 Ci/mmole) and 2.5 units of DNA-polymerase I (Boehringer) at 15° C. for 45 min. The unreacted deoxynucleoside triphosphates were removed by gel filtration over Sephadex G-75 in TE buffer. The highly $^{32}$P-labelled DNA was precipitated with 0.1 vol of 2M sodium acetate (pH 5.1) and 2.5 vol of ethanol at 20° C.

Hybridization of the above probe to the filter impregnated DNA was carried out essentially as described by D. Hanahan and M. Meselson, "Plasmid Screening At High Colony Density", *Gene*, 10, pp. 63–67 (1980). The filters, prepared above, were preincubated for 2 h at 68° C. in 0.1% Ficoll, 0.1% polyvinylpyrrolidone, 0.1% bovine serum albumin, 0.15M NaCl, 0.03M Tris-HCl (pH 8), 1 mM EDTA, and rinsed with 0.02% Ficoll, 0.02% polyvinylpyrrolidone, 0.02% bovine serum albumin, 0.75M NaCl, 0.15M Tris-HCl (pH 8), 5 mM EDTA and 0.5% SDS. The hybridization proceeded overnight at 68° C. in a solution identical to the rinsing solution above using the $^{32}$P-labelled probe which had been denatured at 100° C. for 5 min prior to use. The hybridized filters were washed twice with 0.3M NaCl, 0.06M Tris-HCl (pH 8), 2 mM EDTA for 2 h at 68° C. before air drying and autoradiography.

About 2300 clones originating from cDNA fraction g3 and 880 clones originating from cDNA fraction g2 were screened. As a result of this colony hybridization screening, we identified 8 colonies originating from fraction g3 cDNA and one colony originating from fraction g2 cDNA that strongly hybridized to the $\gamma_0$ probe. The 8 strongly hybridizing colonies from fraction g3 were designated $\gamma_1$, $\gamma_2$, $\gamma_3$, $\gamma_5$, $\gamma_6$, $\gamma_8$, $\gamma_9$, and $\gamma_{11}$. We also identified two weakly hybridizing colonies from that fraction. These were designated $\gamma_4$ and $\gamma_7$. The single strongly hybridizing colony from fraction g2 was designated $\gamma_{10}$. Subsequent restriction and hybridization analysis demonstrated that colonies $\gamma_4$ and $\gamma_7$; were not related to IFN-$\gamma$. Of the 8 strongly hybridizing colonies from fraction g3, one originated from the original group 1 and one from the original group 15 that had been positive in the initial RNA hybridization assay.

It is, of course, evident that this method of clone screening using the HuIFN-$\gamma$ insert DNA $\gamma_0$ or another DNA insert of a clone identified using that insert, as described above, may be employed equally well on other clones containing DNA sequences arising from recombinant DNA technology, synthesis, natural sources or a combination thereof or clones containing DNA sequences related to any of the above DNA sequences by mutation, including single or multiple base substitutions, insertions, inversions, or deletions. Therefore, such DNA sequences and their identification also fall within this invention. It is also to be understood that DNA sequences, which are not screened by the above DNA sequences, yet which as a result of their arrangement of nucleotides code for the polypeptides coded for by the above DNA sequences also fall within this invention.

In addition, because of the expected homology between the DNA sequence coding for human gamma interferon and the DNA sequence coding for gamma interferon from non-human sources, like mouse, swine, chicken, bovine or dog, the DNA sequences of this invention are useful in the selection of the DNA coding for those non-human gamma interferons and in the cloning and expression of those nonhuman interferons for use in non-human antiviral methods and agents.

EXPRESSION OF POLYPEPTIDES DISPLAYING HuIFN-γ ACTIVITY

In order to prepare kidney cells of the African Green Monkey (AP8) for transfection with plasmids containing an IFN-γ-related insert-DNA, we maintained the cells in Dubbecco's modified Eagle's minimal medium ("DME") (GIBCO). The medium contained 10% newborn calf serum (GIBCO), 100 units of penicillin per ml and 100 μg of streptomycin per ml. The cell cultures were transformed with plasmid DNA using a modification of the DEAE-dextran method. The following steps were carried out: the confluent cell monolayers were treated exhaustively with trypsin-EDTA for about 1 h and were then dispersed on 17 mm wells (24 wells per plate; Costar) in DME containing 10% newborn calf serum. After 24 h, the cells were washed two times with HEPES buffered minimal essential medium, and the plasmid DNA (dissolved at about 1–10 μg/μl in 12 μl F11-HEPES buffer) was added to 120 μl DME containing 500 μg/ml DEAE-dextran (Pharmacia). This mixture was then applied to the cell monolayers for about 30–60 min (J. H. McCutchan and J. S. Pagano, "Enhancement Of The Infectivity Of Simian Virus 40 Deoxyribonucleic Acid With Diethylaminoethyl-Dextran", *J. Natl. Cancer Institute*, 41, pp. 351–57 (1978); G. Chu and P. A. Sharp, "SV40 DNA Transfection Of Cells In Suspension: Analysis Of The Efficiency Of Transcription And Translation Of T-Antigen", *Gene*, 13, pp. 197–202 (1981)). After the cells had been washed three times with DME, fresh medium (DME+10% calf serum+100 pg/ml penicillin and 100 μg/ml streptomycin) was added, and the cell cultures were incubated at 37° C. in a $CO_2$ incubator for 72 h.

The plasmid DNA, used for the transfection, was prepared from *E. coli* DH1 (λ) colonies by a lysozyme-detergent lysis and purified by isodensity centrifugation in CsCl gradients in the presence of ethidium bromide essentially as described by M. Kahn et al., "Plasmid Cloning Vehicles Derived From Plasmids ColE1", in *Methods in Enzymology*, 68, *Recombinant DNA*, pp. 268–80 (R. Wu, ed. 1979).

After incubation for 72 h, the supernatant (~½ ml) was removed from the transformed cells and employed in a conventional interferon assay to determine the presence of biologically active IFN-γ-related polypeptides in the supernatant.

As before, the interferon activity produced by the transformed cells was determined on human trisomic (T21) cells challenged with EMC virus. The T21 cells were seeded in Falcon's 96-well microtiter plates one day before use. One hundred microliters of a solution of 60 μl of supernatant and 120 μl of medium was then placed in the first well and 100 μl of serial dilutions of that solution ($log_{10}$=0.5) placed in succeeding wells. EMC virus was added to the wells 20 h later. We evaluated the wells under a light microscope or after staining with crystal violet for inhibition of the virus-induced cytopathic effect.

In order to characterize the IFN-γ activity produced in accordance with this invention more fully a 60 μl aliquot of supernatant from the transformed monkey cells was mixed with 120 μl of medium and 10 μl of IFN-γ antiserum (mouse, 1/5 dilution) and incubated at 37° C. for 2 h. After centrifugation at 1200 g for 5 min, the supernatant was also assayed on T21 cells, as above.

The results of these assays for those clones whose inserts, as determined by restriction analysis and sizing, were the longest ($\gamma_1$, $\gamma_5$ and $\gamma_{10}$) were as follows:

| Plasmid | IFN-γ Activity (Lab. Unit/ml) | IFN-γ Activity After Neutralization With Anti-IFN-γ |
|---|---|---|
| pHIIF-SV-$\gamma_1$ | 100 | 0 |
| pHIIF-SV-$\gamma_5$ | 0 | 0 |
| pHIIF-SV-$\gamma_{10}$ | 0 | 0 |

The above $\gamma_1$ activity amounted to three and one-half wells of antiviral protection; this protection disappearing if the samples were first treated with anti-IFN-γ. Restriction analysis demonstrated that insert-DNA $\gamma_5$ and $\gamma_{10}$ were in the opposite orientations to insert-DNA $\gamma_5$ and pSV529. Therefore, as observed, no activity should have been expressed by hosts transformed with $\gamma_5$ and $\gamma_{10}$. It should, of course, be understood that if the insert DNA $\gamma_5$ and $\gamma_{10}$ are placed in the correct orientation by conventional methods, hosts transformed with those DNA inserts will express IFN-γ.

We also performed neutralization assays using anti-IFN-α (sheep), anti-IFN-β (goat), anti-IFN-γ (mice) and anti-IFN-γ (rabbit). The results were as follows:

| Interferon Source | Neutralization With Anti-IFN | IFN Activity (Lab. Units/ml) |
|---|---|---|
| IFN-α (authentic) | — | 30 |
| IFN-α (authentic) | anti-IFN-α | <3 |
| IFN-β (authentic) | — | 300 |
| IFN-β (authentic) | anti-IFN-β (goat) | <3 |
| IFN-γ (authentic) | — | 100 |
| IFN-γ (authentic) | anti-IFN-γ (mice) | <3 |
| IFN-γ (authentic) | anti-IFN-γ (rabbit) | <3 |
| IFN-γ (pHIIF-SV-$\gamma_1$) | — | 100 |
| IFN-γ (pHIIF-SV-$\gamma_1$) | anti-IFN-γ (mice) | <3 |
| IFN-γ (pHIIF-SV-$\gamma_1$) | anti-IFN-γ (rabbit) | <3 |
| IFN-γ (pHIIF-SV-$\gamma_1$) | anti-IFN-α (sheep) | 100 |
| IFN-γ (pHIIF-SV-$\gamma_1$) | anti-IFN-β (goat) | 160 |

These neutralization assays demonstrated that the biological activity of the polypeptide produced by pHIIF-SV-$\gamma_1$ is neutralized by anti-IFN-γ from two sources (rabbit and mice), but that activity is not neutralized by anti-IFNα or anti-IFN-β. The control assays and those performed previously (supra, p. 20) demonstrated that this difference in antigenic activity parallels the behavior of authentic IFN-α, IFN-β and IFN-γ.

Since nucleotide sequencing (infra) demonstrated that the IFN-γ coding region of $\gamma_1$ also contained nucleotides coding for the presumptive signal sequence of IFN-γ, it is likely that processing of the protein during its excretion into the medium o the eukaryotic cell is occurring.

CHARACTERIZATION OF IFN-γ RELATED INSERT DNA

Figure 6:
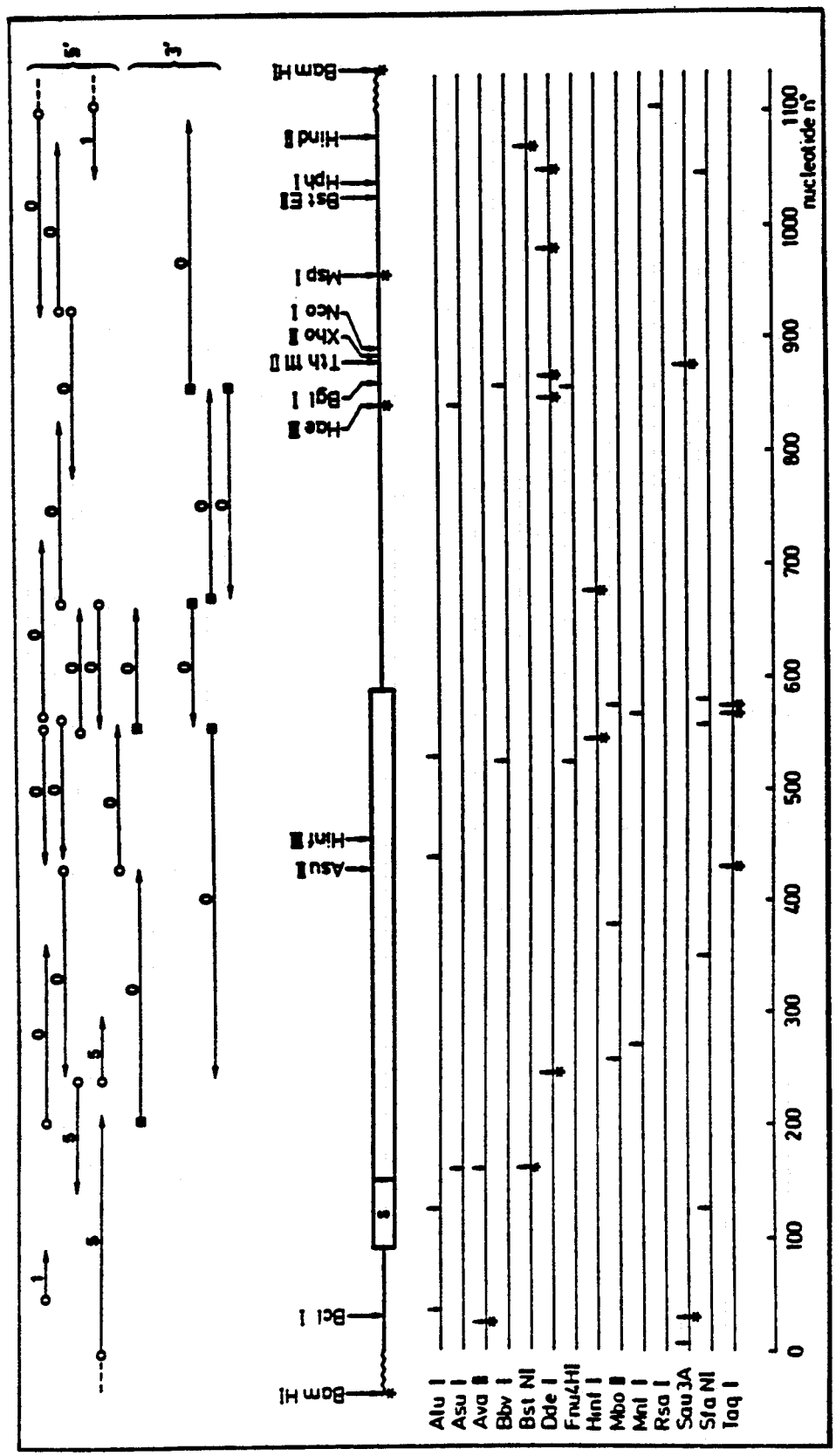
FIG. 6 displays a restriction map of the HuIFN-γ gene of this invention and the sequencing strategy used in sequencing insert DNA γ$_{0(0)}$, γ$_{1(1)}$ and γ$_{5(5)}$. The asterisks (*) indicate restriction sites that we have experimentally determined. The remaining sites were predicted on the basis of the nucleotide sequence.

Referring now to FIG. 6, physical maps of insert DNAs γ₀, γ₁ and γ₅, were constructed by digestion with various restriction enzymes (New England Biolabs or Boehringer) under conditions specified by the suppliers. The products of digestion were electrophoresed in 2.2% agarose or 6% polyacrylamide gels in 40 mM Tris-HOAc (pH 7.8), 20 mM EDTA. They were analyzed after visualization by staining with ethidium bromide or after autoradiography where the restriction fragments were terminally labelled with $^{32}$P-phosphate (infra) and compared with the detailed physical map of pBR322 (J. G. Sutcliffe, "Complete Nucleotide Sequence Of The *Escherichia coli* Plasmid pBR322", *Cold Spring Harbor Symposium*, 43, I, pp. 77–90 (1978)). Restriction maps of the two inserts were constructed on the basis of these digestion patterns. These were refined by sequencing the DNA inserts, substantially by the procedure of A. M. Maxam and W. Gilbert, "A New Method For Sequencing DNA", *Proc. Natl. Acad. Sci. USA*, 74, pp. 560–64 (1977).

Plasmid DNA was prepared from pHIIF-SV-γ₀, pHIIF-SV-γ₁, and pHIIF-SV-γ₅ by the method of Kahn et al. (supra), employed previously herein to isolate the DNA from the sets of clones for screening. The isolated form I DNA was purified by neutral sucrose-gradient centrifugation as before and restricted by various restriction enzymes, essentially as recommended by the supplier (New England Biolabs).

Restricted DNA was dephosphorylated for 30 min at 65° C. in the presence of 4 units bacterial alkaline phosphatase and 0.1% SDS. Following two phenol extractions and ethanol precipitation, the DNA was 5'-terminally labelled with γ-$^{32}$P-ATP (~3000 Ci/mmole) and polynuoleotide kinase (P-L Biochemicals, Inc.). Alternatively, restriction fragments were 3'-terminally labelled by limited DNA-polymerase reaction (Klenow fragment, Boehringer) in the presence of an α-labelled $^{32}$P-nucleoside triphosphate (~1000 Ci/mmole).

For sequencing, labelled fragments were handled in two ways. Some were purified on a polyacrylamide gel prior to cleavage with a second restriction enzyme. Others were immediately cleaved with a second restriction enzyme. In a third procedure the two strands were separated by alkaline denaturation followed by polyacrylamide gel electrophoresis. In both cases the desired fragments were separated on a polyacrylamide gel in Trisborate-EDTA buffer. FIG. 6 displays the various restriction fragments (the circles indicating the label and the arrow the direction of sequencing) and the sequencing strategy employed using pHIIF-SV-γ₀pHIIF-SV-γ₁, and pHIIF-SV-γ₅.

The fragments were degraded according to the method of A. M. Maxam and W. Gilbert (supra). The products were fractionated on polyacrylamide gels of various concentrations and lengths in 50 mM Tris-borate, 1 mM EDTA (pH 8.3) at 900 V to 2000 V.

Each stretch of cDNA insert was sequenced from both strands and each restriction site which served as labelled terminus was sequenced using a fragment spanning it. The composite nucleotide sequence thus obtained for the coding strand of IFN-γ DNA of this invention and its corresponding amino acid sequence is depicted in FIG. 7.

Referring now to FIGS. 7–8, the heteropolymeric part of the insert is flanked on one side by a segment rich in G's and A's (probably reflecting the poly A terminus of the mRNA). For reference the insert is numbered from first nucleotide of the composite insert to a nucleotide well into the untranslated section of that composite insert. An ATG initiation triplet at position 89–91 and a TAA termination triplet at position 587–589 define a reading frame uninterrupted by nonsense codons. Any other translatable sequence, i.e., in different reading frames, flanked by a start signal and a termination signal is too short to code for a polypeptide of the expected size of IFN-γ. Therefore, the region between nucleotides 89 and 586 most likely includes the nucleotide sequence that codes for IFN-γ in accordance with this invention.

This sequence does not exclude the possibility that modifications to the gene such as mutations, including single or multiple, base substitutions, deletions, insertions, or inversions may not have already occurred in the gene or may not be employed subsequently to modify its properties or the properties of the polypeptides expressed therefrom. Nor does it exclude any polymorphism which may result in physiologically similar but structurally slightly different genes or polypeptides than that reported in FIGS. 7–8 (supra).

It should, of course, be understood that cloned cDNA from poly(A) RNA by the usual procedures (supra) may lack 5'-terminal nucleotides and may even contain artifactual sequences (R. I. Richards et al., "Molecular Cloning And Sequence Analysis Of Adult Chicken 8-Globin cDNA", *Nucleic Acids Research*, 7, pp. 1137–46 (1979)). Therefore, it is not certain that the ATG located at nucleotides 89–91 is in fact the first ATG of authentic IFN-γ coding sequence. However, for the purposes of the following description, it is assumed that the ATG at nucleotides 89–91 is the first ATG of authentic IFN-γ coding sequence.

In addition, in eukaryotic mRNAs the first AUG triplet from the 5' terminus is usually the initiation site for protein synthesis (M. Kozak, "How Do Eukaryotic Ribosomes Select Initiation Regions In Messenger RNA?", *Cell*, 15, pp. 1109–25 (1978)). Here, the codon in the composite fragment corresponding to the first amino acid of gamma interferon is 20 codons from the first ATG. This suggests that the DNA sequence coding for gamma interferon may be preceded by a sequence determining a signal polypeptide of 20 amino acids. This presumptive signal sequence contains a series of hydrophobic amino acids. Such accumulation of hydrophobic residues is, of course, characteristic of signal sequences (cf., B. D. David and P. C. Tai, "The Mechanism Of Protein Secretion Across Membranes", *Nature*, 283, pp. 433–38 (1980)).

The nucleotide sequence apparently corresponding to "mature" HuIFN-γ comprises nucleotides, which code for 146 amino acids. The codon usage within the interferon coding sequence is in reasonable agreement with that compiled for mammalian mRNAs in general (R. Grantham et al., "Coding Catalog Usage And The Genome Hypothesis", *Nucleic Acids Research*, 8, pp. 49–62 (1980)).

The structure of the polypeptide depicted in FIG. 7, of course, does not take into account any modifications to the polypeptide caused by its interaction with in vivo enzymes, e.g., glycosylation. Therefore, it must be understood that the amino acid sequence depicted in FIG. 7 may not be identical with HuIFN-γ produced in vivo.

IDENTIFICATION OF A CHROMOSOMAL GENE CODING FOR HuIFN-γ

A collection of hybrid phage derived from fragments of fetal human chromosomal DNA which had been generated by partial cleavage with HaeIII and AluI, and joined with EcoRI linkers to λ Charon 4A arms has been prepared by R. M. Lawn et al., *Cell*, 15, pp. 1157-74 (1978). This gene bank was screened by an "in situ" procedure (W. D. Benton and R. W. Davis, *Science*, 196, pp. 180-82 (1977); T. Maniatis et al., *Cell*, 15, pp. 687-701 (1978)); using as a probe the $^{32}$P-labelled DNA insert described previously. Two hybridization-positive phage clones were isolated from 800,000 plaques by repeated plaque purification (T. Maniatis et al., supra). These plaques were designated λCH4A-gHIIF-1 and λCH4A-gHIIF-2.

Both λCH4A-gHIIF-1 and λCH4A-gHIIF-2 produced IFN-γ activity when injected into oocytes. Restriction analysis demonstrated that the two plaques were different in that λCH4A-gHIIF-1 was shorter at its 3' end than λCH4A-gHIIF-2. However, since both plaques were biologically active, it appears that the missing sequence in λCH4A-gHIIF-1 is not part of the IFN-γ coding sequence or at least that part encoding biological activity.

Restriction analysis of λCH4A-γHIIF-1 and λCH4A-gHIIF-2 also demonstrated that they contained introns within the coding sequence for IFN-γ. However, the positive biological activity of the plaques demonstrates that the genes are correctly processed in *Xenopus laevis*.

IMPROVING THE YIELD AND ACTIVITY OF POLYPEPTIDES DISPLAYING HuIFN-γ ACTIVITY PRODUCED IN ACCORDANCE WITH THIS INVENTION

The level of production of a protein is governed by three major factors: the number of copies of its gene within the cell, the efficiency with which those gene copies are transcribed and the efficiency with which they are translated. Efficiency of transcription and translation (which together comprise expression) is in turn dependent upon nucleotide sequences, normally situated ahead of the desired coding sequence. These nucleotide sequences or expression control sequences define, inter alia, the location at which RNA polymerase interacts to initiate transcription (the promoter sequence) and at which ribosomes bind and interact with the mRNA (the product of transcription) to initiate translation. Not all such expression control sequences function with equal efficiency. It is thus of advantage to separate the specific coding sequences for the desired protein from their adjacent nucleotide sequences and to fuse them instead to other known expression control sequences so as to favor higher levels of expression. This having been achieved, the newly engineered DNA fragments may be inserted into higher copy number plasmids or bacteriophage derivatives in order to increase the number of gene copies within the cell and thereby further to improve the yield of expressed protein.

Several expression control sequences may be employed as described above. These include the operator, promoter and ribosome binding and interaction sequences (including sequences such as the Shine-Dalgarno sequences) of the lactose operon of *E. coli* ("the lac system"), the corresponding sequences of the tryptophan synthetase system of *E. coli* ("the trp system"), the major operator and promoter regions of phage λ ($O_LP_L$, as described above, and $O_RP_R$), a control region of filamentous single-stranded DNA phages, or other sequences which control the expression of genes of prokaryotic or eukaryotic cells and their viruses or combinations thereof. Therefore, to improve the production of a particular polypeptide in an appropriate host, the gene coding for that polypeptide may be prepared as before and inserted into a recombinant DNA molecule closer to its former expression control sequence or under the control of one of the above improved expression control sequences. Such methods are known in the art.

Other methods to improve the efficiency of translation involve insertion of chemically or enzymatically prepared oligonucleotides in front of the initiating codon. By this procedure a more optimal primary and secondary structure of the messenger RNA can be obtained. More specifically, a sequence can be so designed that the initiating AUG codon occurs in a readily accessible position (i.e., not masked by secondary structure) either at the top of a hairpin or in other single-stranded regions. Also the position and sequence of the aforementioned Shine-Dalgarno segment can likewise be optimized. The importance of the general structure (folding) of the messenger RNA has been documented (D. Iserentant and W. Fiers "Secondary Structure Of mRNA And Efficiency Of Translation Initiation", *Gene*, 9, 1-12 (1980)).

Further increases in the cellular yield of the desired products depend upon an increase in the number of genes that can be utilized in the cell. This may be achieved by insertion of the IFN-γ gene (with or without its transcription and translation control elements) in a higher copy number plasmid or in a temperature-controlled copy number plasmid (i.e., a plasmid which carries a mutation such that the copy number of the plasmid increases after shifting up the temperature (B. Uhlin et al. "Plasmids With Temperature-Dependent Copy Number For Amplification Of Cloned Genes And Their Products", *Gene*, 6, 91-106 (1979)).

Alternatively, an increase in gene dosage can be achieved for example by insertion of recombinant DNA molecules engineered in the way described previously into the temperate bacteriophage λ, most simply by digestion of the plasmid with a restriction enzyme, to give a linear molecule which is then mixed with a restricted phage λ cloning vehicle (e.g., of the type described by N. E. Murray et al., "Lambdoid Phages That Simplify The Recovery Of In Vitro Recombinants", *Mol. Gen. Genet.*, 150, 53-61 (1977), and N. E. Murray et al., "Molecular Cloning Of The DNA Ligase Gene From Bacteriophage T4", *J. Mol. Biol.*, 132, 493-505 (1979)) and the recombinant DNA molecule produced by incubation with DNA ligase. The desired recombinant phage is then selected as before and used to lysogenize a host strain of *E. coli*.

Therefore, it should be understood that the insert DNA of this invention may be removed from the SV529 plasmid and inserted into other expression vectors, as previously described (supra, pp. 25-28) and these vectors employed in various hosts, as previously described (supra, pp. 25-28) to improve the expression of the gene coding for IFN-γ.

It should also be understood that polypeptides displaying IFN-γ activity (prepared in accordance with this invention) may also be prepared in the form of a fused protein (e.g., linked to a prokaryotic or eukaryotic N-terminal segment directing excretion), in the form of prointerferon (e.g., starting with all or parts of the interferon signal sequence which could be cleaved off upon excretion) or as mature interferon (by cleavage of any extraneous amino acids, including an initial methionine during expression and excretion) or in the form of a f-met-interferon. One particularly useful polypeptide in accordance with this invention would be mature gamma interferon with an easily cleaved amino acid or series of amino acids attached to the amino terminus. Such construction would allow synthesis of the protein in an appropriate host, where a start signal not present in mature gamma interferon is needed, and then cleavage of the extra amino acids to produce mature gamma interferon.

The yield of these different forms of polypeptide may be improved by any or a combination of the procedures discussed above. Also different codons for some or all of the codons used in the present DNA sequences could be substituted. These substituted codons may code for amino acids identical to those coded for by the codons replaced but result in higher yield of the polypeptide. Alternatively, the replacement of one or a combination of codons leading to amino acid replacement or to a longer or shorter HuIFN-γ-related polypeptide may alter its properties in a useful way (e.g., increase the stability, increase the solubility, increase the antiviral activity, increase the 2,5-A synthetase activity or increase the host specificity range). In addition, hybrids with other of the interferons might be prepared on the gene level and expressed in appropriate hosts or on the protein level by chemical synthetic methods.

Finally, the activity of the polypeptides produced by the recombinant DNA molecules of this invention may be improved by fragmenting, modifying or derivatizing the DNA sequences or polypeptides of this invention by well-known means, without departing from the scope of this invention.

One example of a method for improving the yield of the polypeptides of this invention is depicted in FIG. 9. It involved using the $P_L$ temperature-inducible expression system (E. Remaut et al., Gene, 15, pp. 81–93 (1981)). This construction was characterized by an ATG start codon fused directly to the nucleotide triplet (TGT) encoding the first amino acid of mature γ interferon. This construction produces an f-Met-IFN-γ. However, it is to be understood that the initial methionine may be cleaved during expression by the E. coli itself or subsequently removed to produce mature IFN-γ.

The construction was prepared by restricting a plasmid carrying the DNA sequence encoding pre-γ interferon (FIG. 9) (from a dam− strain of E. coli to ensure that any A nucleotide would not be methylated, thereby blocking the AvaII site in that sequence) with AvaII. The resulting fragment, which is missing the first four codons of mature γ-IFN, was ligated to a synthetic linker having the following sequence:

```
AGCTTGTTACTGCCAG
  ACAATGACGGTCCTG
```

This linker caries a HindIII residue at one end, an AvaII residue at the other, and the coding sequence for the first four amino acids of mature γ interferon (TGTTACTGCCAG). The resulting fragment was then cleaved with BamHI (the site for which lies outside of the IFN-γ coding sequence) and inserted between the HindIII and BamHI sites of a plasmid carrying the trp promoter (FIG. 9).

We then cleaved that resulting plasmid with HindIII and EcoRI and removed the overhanging ends with S1. These manipulations resulted in the deletion of an EcoRI-HindIII fragment and the triplet (TGT) coding for the first amino acid of IFN-γ being fused directly behind the ATG start codon generated by the EcoRI restriction and S1 digestion.

To remove the trp promoter from this on vector and to replace it with a $P_L$ promoter, we restricted pPLc236 (described in European patent application 41767) with EcoRI and filled in the residue (Klenow). We then restricted the DNA sequence with BamHI and combined that sequence with the HpaI-BamHI fragment, containing the IFN-γ coding sequence, from the above-described plasmid (FIG. 9).

We then transformed E. coli SG4044 (pc1857), a protease minus strain carrying a temperature sensitive repressor with our IFN-γ-containing $P_L$ expression vector. This transformed strain produced a polypeptide displaying the activity of IFN-γ at a level of about 15% of total cell protein.

We have also prepared a similar construction using the same DNA sequence and the expression vector pPLc28 (Remaut et al., supra). This construction is less preferred than the former construction because the IFN-γ yield is somewhat less. However, it has better long term stability. Because of its stability, we deposited this latter culture (E. coli K12ΔHIΔtrp (pPLc28-HIIF52)) with the American Type Culture Collection (infra).

Figure 11:
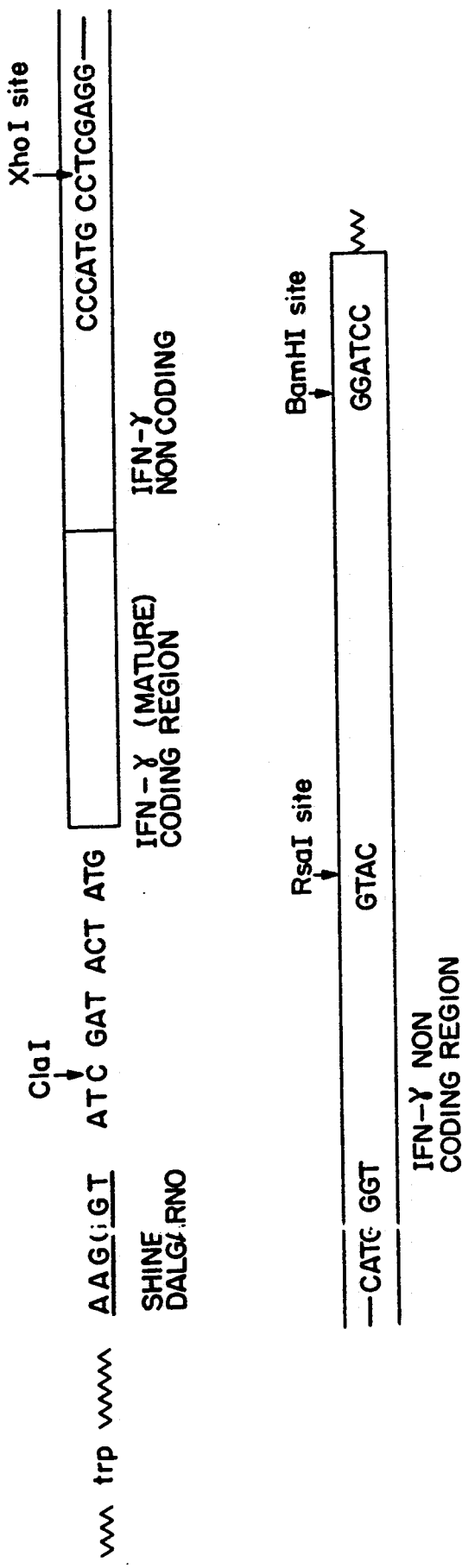
FIG. 11 is a schematic depiction of relevant portions of plasmid per ori γ.
Figure 12:
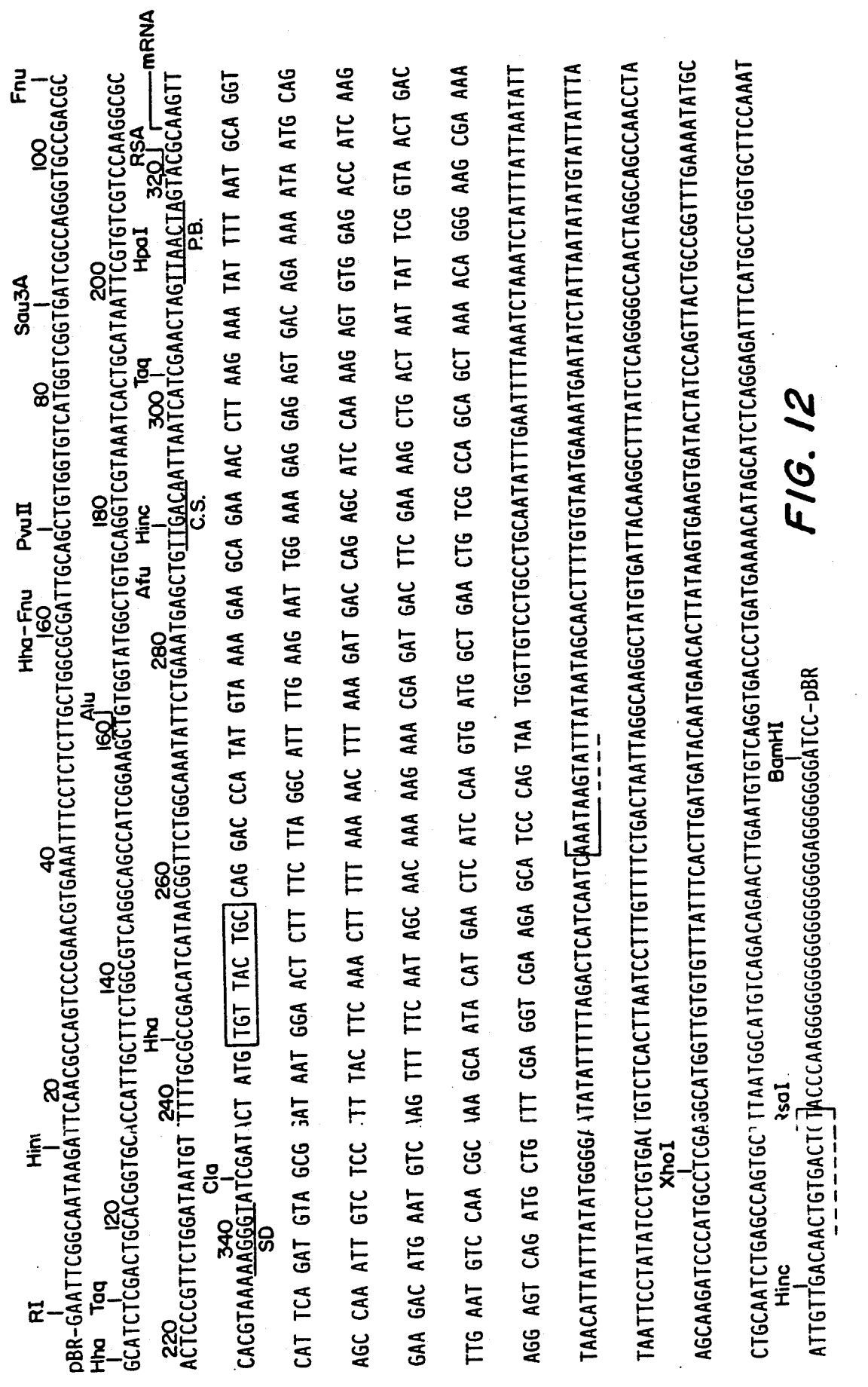

The most preferable method for improving the yield of the polypeptides of this invention is through the use of an expression system comprising a trp-derived expression control sequence. Such an expression system is exemplified by the recombinant expression molecule per ori γ which contains the DNA sequence encoding mature IFN-γ, operatively linked to the operator-promoter region and the Shine-Dalgarno sequence of a trp-derived expression control sequence (see, e.g., FIGS. 11 and 12). This molecule also has a translational start codon (ATG) attached to the coding sequence (TGT) of the first amino acid of mature IFN-γ and contains a ClaI restriction site between the Shine-Dalgarno sequence of the trp expression control sequence and the start codon (FIGS. 11 and 12). More particularly, the region between the Shine-Dalgarno sequence and the start codon consists of nine nucleotide bases having the sequence ATCGATACT. We have discovered that, surprisingly, this nine base sequence results in enhanced expression of DNA sequences encoding IFN-γ operatively linked to the trp-derived expression control sequence as compared with a trp expression control sequence with some other DNA sequence between the Shine-Dalgarno sequence and the IFN-γ start codon (see, e.g., P. Gray et al., "Expression Of Human Immune Interferon cDNA In E. coli And Monkey Cells", Nature, 295, pp. 503–08 (1982).

A bacterial host transformed with per ori γ expressed high levels of IFN-γ which was active in antiviral and antiproliferative assays.

It should, of course, be understood that, while we have described one expression vector containing our trp-derived expression system, other expression vectors containing trp-derived expression control sequences which contain the nine nucleotide sequence ATCGATACT between the Shine-Dalgarno sequence and the translational start signal may be used to express DNA sequences encoding IFN-γ at high levels.

EXPRESSION OF IFN-γ IN ANIMAL CELLS

Although bacterial-produced, and therefore non-glycosylated, IFN-γ is biologically active, human IFN-γ has been shown to be glycosylated (Y. K. Yip et al., *Proc. Natl. Acad. Sci. USA*, 78, pp. 1601–05 (1981)). However, the glycosylated protein has not been fully characterized. It would, therefore be useful to produce glycosylated IFN-γ using the DNA sequences of this invention in animal cells for use in the various therapeutic and clinical methods and compositions described previously.

Several cloning vectors now exist which enable the expression of cloned genes in a heterologous mammalian environment (e.g., P. J. Southern & P. Berg, *J. Mol. Appl. Genet.*, 1, pp 327–41 (1982); S. Subramani et al., *Mol. Cell. Biol.*, 1, pp. 854–64 (1981); R. J. Kaufman & P. A. Sharp, *J. Mol. Biol.*, 159, pp. 601–21 (1982). We chose to use a system involving the co-transformation of Chinese hamster ovary (CHO) cells, deficient in dihydrofolate reductase (DHFR⁻) (G. Urlaub & L. A. Chasin, *Proc. Natl. Acad. Sci. USA*, 77, pp. 4216–20 (1980)) with the two plasmids pAdDSV(A)-3 (R. J. Kaufman & P. A. Sharp, *J. Mol. Biol.*, supra and pSV2-IFN-γ which encodes human IFN-γ (FIG. 10).

We routinely maintained the CHO, DHFR⁻ cells (a gift of P. A. Sharp) used in this co-transformation at 37° C. in tissue culture flasks (Gibco) containing alpha minimal essential medium (MEM) (Gibco, Cat. No. 072-1900), supplemented with 10% fetal calf serum (FCS) and gentamycin (50 μg/ml). We cultured the transformants as above but in alpha MEM (lacking ribonucleosides and deoxyribonucleosides (Gibco, Cat. No. 072-2000)) and 10% dialyzed FCS. This latter medium is referred to as "selective medium".

We prepared the IFN-γ-containing plasmid (pSV2-IFN-γ), used in our expression of glycosylated IFN-γ, by restricting pHIIF-SV-γ₁₀ (R. Devos et al., *Nucleic Acids Research*, 10, pp. 2487–501 (1982)) with Sau3A (the recognition site being located in the 3' non-coding region of IFN-γ) (FIG. 6). We purified the resulting about 850 base pair fragment, containing the IFN-γ, on a sucrose gradient and then ligated it into a partially BamHI-digested pPLc2833 expression vector. Expression vector pPLc2833 is identical to pPLc28 (European patent application 41767), except that we had inserted a synthetic linker (BamHI-XbaI-SalI-XbaI-SalI-XbaI-PstI-BamHI) into the unique BamHI site of pPLc28 (Remaut et al., *Gene*, 15, pp. 81–93 (1981)). We designated the resulting IFN-γ-containing recombinant DNA molecule pPLcSA-IFN-γ.

We then restricted this molecule with HindIII and BamHI to isolate its IFN-γ-containing fragment. We ligated this fragment into a HindIII/BglII-cleaved derivative of pSV2-dhfr, thereby replacing the HindIII/BglII mouse dhfr cDNA-carrying fragment in that plasmid with our IFN-γ-carrying fragment. The modified pSV2-dhfr (a gift of Berg and Canaani) used in this ligation is identical to pSV-2dhfr (S. Subramani et al., *Mol. Cell. Biol.*, 1, pp. 854–64 (1981)) except that the prokaryotic sequence carrying EcoRI-PvuII fragment of pSV2-dhfr has been replaced with an EcoRI-SalI fragment of pML, a deletion mutant of pBR322 that does not contain sequences inhibitory to replication in mammalian cells (M. Lusky & M. Botchan, *Nature*, 293, pp. 79–81 (1981)). The resulting plasmid pSV-IFN-γ, therefore, contains the IFN-γ coding sequence immediately downstream of the SV40 early promoter and upstream of the SV40 splice sites and polyadenylation signal (FIG. 10).

The other plasmid used in our co-transformation was pAdD26SV(A)-3 (a gift of P. Sharp). It contains the mouse DHFR coding sequence (FIG. 10). It transforms cells into a DHFR⁺ phenotype, as demonstrated by the transformant's ability to grow in selective medium (i.e., medium that lacks ribonucleosides and deoxyribonucleosides).

We used a method similar to that described by Graham and van der Eb to cotransform our CHO cells (F. L. Graham & A. J. van der Eb, *Virology*, 54, pp. 536–39 (1973)). We first seeded tissue culture flasks (125 cm²) with 5×10⁵ cells/flask 24 h prior to the addition of the DNA to those cells. We prepared the DNA for addition to the cells by cleaving the two plasmids (described above) with BamHI or EcoRI, combining appropriate quantities of the cleaved DNA (usually about 10 μg in total) in various relative ratios (pSV-IFN-γ:pAdD26SV(A)-3; 1:1, 10:1 and 25:1), precipitating the DNA with ethanol, resuspending it in 200 μl 1 mM Tris-HCl (pH 7.2); 0.1 mM HEPES (pH 7.2) and slowly pipetting the resulting solution into 250 μl (2xHBS:280 mM NaCl; 3.0 mM Na₂HPO₄; 100 mM HEPES (pH 7.2)), while continually aspirating the HBS solution.

After allowing the calcium phosphate-DNA precipitate to form for 30 min at room temperature, we added the 500 μl suspension to a monolayer from which growth medium had been removed. We tilted the flask to ensure dissipation of the precipitate over the entire monolayer.

After the flask was left for 30 min at room temperature, we added 5 ml medium and incubated the flask for 4 h at 37° C. We then treated the cells with medium, containing 10% glycerol, and washed them twice with medium. After about 2 days the cells reached confluency. We then subcultured them (1:10) into selective medium and replenished the selective medium at five day intervals until after approximately two weeks we were able to observe single colonies. We trypsinized these presumed transformants in cloning cylinders and transferred them to small flasks (25 cm²).

Initially we isolated 135 transformants from the six types of co-transformations (EcoRI/BamHI—each at DNA ratios of 1:1, 10:1 and 25:1). We screened samples of the culture medium from the monolayers of these transformants to detect those transformants which were constitutively secreting interferon.

These assays were based on the ability of γ interferon to inhibit the cytopathic effect of encephalomyocarditis virus (EMC) on human FS-4 fibroblast cells. For the assay we prepared serial dilutions (1:3) of the samples in growth medium and transferred them to 8×12-well microtiter plates, containing sub-confluent monolayers of FS-4 cells. After a 24 h incubation at 37° C., we replaced the growth medium and added aliquots of EMC to each well. We read the plates after 24 h further incubation and scored the individual wells according to the degree of protection against the cytopathic effects of the virus conferred upon the cells. We also used a stock solution of IFN-γ on each plate as an internal standard. We express our assay results as "laboratory units", the reciprocal of the dilution which causes a 50% inhibition of the cytopathic effect. We have compared our "laboratory unit" with the National Institutes of Health human leukocyte reference interferon (G-023-901-527). One IFN-α international unit is approximately equivalent to 10 IFN-γ "laboratory units" in our assay system.

We also used four types of control transformants in our assays—EcoRI and BamHI digestions of the individual plasmids pSV2-IFN-γ and pAdD26SV(A)-3. We obtained no DHFR+ transformants using any of these controls. Furthermore, transformants using digested pAdD26SV(A)-3 DNA alone produced no detectable interferon activity.

The results of these assays are set forth in Table 1.

TABLE I

| Molecular Ratio[1] | Restriction Enzyme | Number of Transformants[2] | | |
|---|---|---|---|---|
| | | >100 | <100 | 0 |
| 25:1 | EcoRI | 4 | 2 | 3 |
| | BamHI | 1 | 3 | 1 |
| 10:1 | EcoRI | 12 | 1 | 0 |
| | BamHI | 16 | 14 | 5 |
| 1:1 | EcoRI | 12 | 13 | 13 |
| | BamHI | 16 | 6 | 13 |

[1]pSV2-IFN-γ/pAdD26SV(A)-3
[2]This records the number of transformants that produce a certain level of IFN-γ. The results are expressed in laboratory units/ml.

We selected two of the highest producing transformants and designated them E-10B and E-10C, because they had both been prepared using EcoRI and the 10:1 DNA ratio. However, the two-day cell incubation in non-selective medium prior to selection of transformants may have caused the isolated transformants to have been derived from a low number of transformed cells. Therefore, the significance of the particular DNA ratio is uncertain.

These cell lines produced about 50,000 lab units/ml of IFN-γ. This compares favorably with HuIFN-γ production by classical methods of stimulating lymphocytes and has the further advantage that it is constitutive and does not therefore require induction. Production of IFN-γ by the methods of the present invention is also advantaged because here the IFN-γ will not be contaminated with other lymphokines as is the case in conventional IFN-γ production by induction of cell cultures.

E-10B3 and E-10C6 (purified sub-lines from recloning single colonies of E-10B and E-10C) behaved differently during prolonged growth. E-10B3 had a significant decrease in IFN-γ production between passages 15 and 20. However, we observed no such decrease in IFN-γ production using E-10C6. In addition, another cell line derived from E-10C as a single colony, when grown in 10 nM methotrexate (MTX) produced IFN-γ at an approximately 6X higher level than E-10C. We have also grown a colony selected after growth in 10 nM methotrexate (E-10C101) in 250 nM MTX (E-10C101-250 nM). A confluent monolayer of 170 cm² of these cells grown in 50 ml medium yielded $3 \times 10^5$ laboratory units of IFN-γ/ml of culture (sp. activity: $2-4 \cdot 10^7$ (lab units/mg)). We deposited this cell culture (Chinese Hamster Ovary Cell (DHFR−) (R10C101 250 nM)) with the American Type Culture Collection (the "R" being instead of the "C" to designate EcoRI digestion). Further amplification and production increases should be possible using methotrexate and other amplification methods. In addition, cells may be selected for growth in high levels of IFN-γ to avoid any possible toxicity problems with overproducing strains and for growth in lower percentages of serum (e.g., 0.5% vs. 5%) to reduce culture costs.

Initial estimates of the molecular weight of nature IFN-γ (determined by gel filtration techniques) have varied between 40,000 and 60,000 (e.g., Y. K. Yip, Proc. Natl. Acad. Sci. USA, 78, pp. 1601–05 (1981); M. P. Langford et al., Infect. Immun., 26, pp. 36–41 (1979)). More recently, molecular weight estimates of 25,000 and 20,000 have been made (Y. K. Yip et al., Proc. Natl. Acad. Sci. USA, 79, pp. 1820–24 (1982)). These recent estimates suggest that IFN-γ may be an aggregate, possibly a dimer, composed of identical or non-identical 20,000 and 25,000 subunits. Our CHO produced IFN-γ (cell line E-10C101) was two species of molecular weight 21,000 and 25,000 daltons, respectively. These species must arise from the single cloned gene of pSV2-IFN-γ. Because the molecular weight of bacterially (non-glycosylated) IFN-γ is about 17,000 and because there are two possible sites for glycosylation in the polypeptide, it may be that the three forms of IFN-γ are the non-glycosylated (17,000) and two differentially glycosylated (21,000 and 25,000) species.

The IFN-γ produced in our CHO cells was immunoprecipitated with mouse anti-Hu-IFN-γ serum produced by immunization of a Balb/C mouse with the 45 K Hu-IFN-γ peak from an AcA 54 gel filtration column, following the induction of human splenocytes with staphylococcal enterotoxin A (R. Devos et al., J. Interferon Res., 2, pp. 409–420 (1982)). We also observed the two molecular weight bands in samples that had been immunoprecipitated with anti-Hu-IFN-γ, thereby further confirming their identity.

After purification by a variety of means from the cell cultures, the glycosylated IFN-γ produced in this invention may be used in the various clinical and therapeutic applications of IFN-γ previously described. In addition, both the abovedescribed glycosylated IFN-γ and the previouslydescribed non-glycosylated IFN-γ may be used to interrupt the immune cascade in, for example, allograft rejection or used in place of or as equivalent to macrophage activation factor (MAF) in the treatment of persistent bacterial or parasitic infections.

As an interrupter of the immune cascade, IFN-γ would be useful in preventing allograft rejection. For example, it is known that foreign cells (e.g., a transplanted tissue) and their antigens stimulate the T-cells of the host to make lymphokines. Therefore, locally around the allograft, lymphokines, including IFN-γ, will be produced in response to the foreign tissue. The IFN-γ then may act on the foreign cells to stimulate those cells to make Ia determinants. The foreign determinants and the foreign antigens will then be presented in the proper context to the host to cause a vigorous immune reaction, leading to the production of antibodies in the host against the foreign antigens, and more importantly the production of cytotoxic T-cells to reject the graft. It is one aspect of this invention to use antibodies to IFN-γ of this invention to prevent such rejection because such antibodies will bind with the IFN-γ made by the host T-cells during stimulation by the foreign cells and antigens. That bound IFN-γ will then not be available to stimulate the foreign cells to make Ia determinants and thereby prevent presentation of the antigens and determinants in the proper context to the host to generate cytotoxic T-cells and cause the rejection by the host of the foreign tissue.

As a replacement, or perhaps equivalent to MAF, the IFN-γ of this invention would activate macrophages to kill cells, e.g., tumors, and take up bacterial viruses and small particulate matter, e.g., parasites. In this application IFN-γ would be especially useful in treating bacterial infections that are resistant to antibiotics.

Microorganisms and recombinant DNA molecules prepared by the processes described herein are exemplied by cultures deposited in the culture collection of the American Type Culture Collection, Rockville, Maryland on Feb. 19, 1982. These cultures have been identified there as follows:

HIIF-A: *E. coli* DH1(λ)(pHIIF-SV-γ₁)
HIIF-B: *E. coli* DH1(λ)(pHIIF-SV-γ₅)
HIIF-C: λCH4A-gHIIF-2

These cultures have been assigned accession numbers ATCC 39046, 39047 and 40044, respectively.

In addition, two other transformed hosts carrying recombinant DNA molecules prepared by the processes described herein are exemplified by cultures deposited in the culture collection of the American Type Culture Collection, Rockville, Maryland on Jan. 27, 1983. These cultures are identified as follows:

HIIF-D: Chinese Hamster Ovary Cells (DHFR⁻) (R10C101-250 nM)
HIIF-E: *E. coli* K12ΔHIΔtrp (pPLc28-HIIF 52)

These cultures have been assigned accession numbers ATCC CRL 8200 and 39278, respectively.

While we have hereinbefore presented a number of embodiments of this invention, it is apparent that our basic construction can be altered to provide other embodiments which utilize the processes and compositions of this invention. Therefore, it will be appreciated that the scope of this invention is to be defined by the claims appended hereto rather than by the specific embodiments which have been presented hereinbefore by way of example.

What is claimed is:

1. An expression vector for producing IFN-γ type polypeptides in hosts transformed with it comprising a DNA sequence encoding a polypeptide of the IFN-γ type, said DNA sequence being operatively linked to an expression control sequence comprising the promoter-operator regions and Shine-Dalgarno sequence of a trp operon and further comprising the DNA sequence ATCGATACT between the Shine-Dalgarno sequence and the translational start sequence of the DNA sequence encoding a polypeptide of the IFN-γ type.

2. The expression vector according to claim 1, wherein the expression control sequence comprises:

GGTGTCATGGTCGGTGATCGCCAGGGTGCCGACGCGC
ATCTCGACTGCACGGTGCACCAATGCTTCTGGCGTCA
GGCAGCCATCGGAAGCTGTGGTATGGCTGTGCAGGTC
GTAAATCACTGCATAATTCGTGTCGCTCAAGGCGCAC
TCCCGTTCTGGATAATGTTTTTTGCGCCGACATCATAA
CGGTTCTGGCAAATATTCTGAAATGAGCTGTTGACAA
TTAATCATCGAACTAGTTAACTAGTACGCAAGTTCACG
TAAAAAGGGTATCGATACT.

3. The expression vector of claim 1 which includes the DNA sequence depicted in FIG. 12.

4. A host cell transformed with at least one expression vector according to claim 1.

5. A host cell transformed with at least one expression vector of either of claims 2 or 3.

6. The host of claim 5 which is *E. coli*.

7. A method for producing a polypeptide displaying an immunological or biological activity of human immune interferon, comprising the steps of transforming an appropriate host with an expression vector according to either of claims 2 or 3; culturing said host; and collecting said polypeptide.

8. The method according to claim 7 wherein the host is *E. coli*.

9. A method for producing a polypeptide displaying an immunological or biological activity of human immune interferon comprising the steps of culturing a host transformed by an expression vector according to either of claims 2 or 3 and collecting said polypeptide.

10. A method for producing a polypeptide displaying an immunological or biological activity of human immune interferon, comprising the steps of transforming an appropriate host with an expression vector according to claim 1; culturing said host; and collecting said polypeptide.

11. The method according to claim 10, wherein the host is selected from prokaryotic and eukaryotic cells.

12. A method for producing a polypeptide displaying an immunological or biological activity of human immune interferon comprising the steps of culturing a host transformed by an expression vector according to claim 1 and collecting said polypeptide.

* * * * *